United States Patent
Kleshinski et al.

(10) Patent No.: US 11,490,896 B2
(45) Date of Patent: Nov. 8, 2022

(54) DELIVERY AND DETACHMENT MECHANISMS FOR VASCULAR IMPLANTS

(71) Applicant: Covidien LP, Mansfield, MA (US)

(72) Inventors: Stephen Kleshinski, Fremont, CA (US); Karl Halden, San Carlos, CA (US)

(73) Assignee: COVIDIEN LP, Mansfield, MA (US)

( * ) Notice: Subject to any disclaimer, the term of this patent is extended or adjusted under 35 U.S.C. 154(b) by 224 days.

(21) Appl. No.: 16/946,975

(22) Filed: Jul. 14, 2020

(65) Prior Publication Data

US 2020/0337709 A1 Oct. 29, 2020

Related U.S. Application Data

(63) Continuation of application No. 16/103,448, filed on Aug. 14, 2018, now Pat. No. 10,743,882, which is a
(Continued)

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12145* (2013.01);
(Continued)

(58) Field of Classification Search
CPC ........ A61B 17/12022; A61B 17/12027; A61B 17/12031; A61B 17/12099; A61B 17/12109; A61B 17/12113; A61B 17/12118; A61B 17/12131; A61B 17/1214; A61B 17/12145; A61B 17/1215; A61B 17/12168; A61B 17/12172;
(Continued)

(56) References Cited

U.S. PATENT DOCUMENTS

| 4,655,219 A | 4/1987 | Petruzzi |
| 5,109,867 A | 5/1992 | Twyford |

(Continued)

FOREIGN PATENT DOCUMENTS

| CN | 2456640 Y | 10/2001 |
| CN | 1652726 A | 8/2005 |

(Continued)

OTHER PUBLICATIONS

Hill, et al., "Initial Results of the Amplatzer Vascular Plug in the Treatment of Congenital Heart Disease, Business Briefing", US Cardiology 2004.
(Continued)

*Primary Examiner* — Ryan J. Severson
(74) *Attorney, Agent, or Firm* — Fortem IP LLP; Matthew Lincicum

(57) ABSTRACT

Vascular delivery systems configured to deliver an implant to a location within a vasculature can include one or more control wires controllable by a user to detach the implant from the delivery system. Control wires can cause a feature of the delivery system to mechanically engage a hub at a proximal end of an implant. Proximal or distal movement of the control wire can allow the feature to disengage from the hub, thereby allowing release of the implant.

20 Claims, 15 Drawing Sheets

Related U.S. Application Data continuation of application No. 14/776,815, filed as application No. PCT/US2014/029647 on Mar. 14, 2014, now Pat. No. 10,076,336.

(60) Provisional application No. 61/792,147, filed on Mar. 15, 2013.

(52) U.S. Cl.
CPC ... *A61B 17/12172* (2013.01); *A61B 17/12118* (2013.01); *A61B 2017/00853* (2013.01); *A61B 2017/1205* (2013.01); *A61B 2017/12054* (2013.01); *A61B 2017/12086* (2013.01)

(58) Field of Classification Search
CPC .... A61B 17/12177; A61B 2017/00853; A61B 2017/1205; A61B 2017/12054; A61B 2017/12086
See application file for complete search history.

(56) References Cited

U.S. PATENT DOCUMENTS

| | | | |
|---|---|---|---|
| 5,217,484 A | 6/1993 | Marks | |
| 5,234,437 A | 8/1993 | Sepetka | |
| 5,250,071 A | 10/1993 | Palermo | |
| 5,261,916 A | 11/1993 | Engelson | |
| 5,263,964 A | 11/1993 | Purdy | |
| 5,282,806 A | 2/1994 | Haber et al. | |
| 5,304,195 A | 4/1994 | Twyford et al. | |
| 5,312,415 A | 5/1994 | Palermo | |
| 5,334,210 A | 8/1994 | Gianturco | |
| 5,350,397 A | 9/1994 | Palermo et al. | |
| 5,354,295 A | 10/1994 | Guglielmi et al. | |
| 5,368,592 A | 11/1994 | Stern et al. | |
| 5,417,708 A | 5/1995 | Hall et al. | |
| 5,480,382 A | 1/1996 | Hammerslag et al. | |
| 5,490,859 A | 2/1996 | Mische et al. | |
| 5,499,985 A | 3/1996 | Hein et al. | |
| 5,562,698 A | 10/1996 | Parker | |
| 5,601,600 A * | 2/1997 | Ton | A61B 17/12022 606/198 |
| 5,669,905 A | 9/1997 | Scheldrup et al. | |
| 5,669,931 A | 9/1997 | Kupiecki et al. | |
| 5,728,129 A | 3/1998 | Summers | |
| 5,746,769 A | 5/1998 | Ton et al. | |
| 5,782,747 A | 7/1998 | Zimmon | |
| 5,800,455 A | 9/1998 | Palermo et al. | |
| 5,814,062 A | 9/1998 | Sepetka et al. | |
| 5,895,391 A | 4/1999 | Farnholtz | |
| 5,951,599 A | 9/1999 | McCrory | |
| 5,989,242 A | 11/1999 | Saadat et al. | |
| 6,004,338 A | 12/1999 | Ken et al. | |
| 6,022,369 A | 2/2000 | Jacobsen et al. | |
| 6,039,744 A | 3/2000 | Forber | |
| 6,063,070 A | 5/2000 | Eder | |
| 6,136,015 A | 10/2000 | Kurz et al. | |
| 6,152,947 A | 11/2000 | Ambrisco et al. | |
| 6,190,373 B1 | 2/2001 | Palermo et al. | |
| RE37,117 E | 3/2001 | Palermo | |
| 6,203,547 B1 | 3/2001 | Nguyen et al. | |
| 6,245,012 B1 | 6/2001 | Kleshinski | |
| 6,270,508 B1 | 8/2001 | Klieman et al. | |
| 6,277,125 B1 | 8/2001 | Barry et al. | |
| 6,296,622 B1 | 10/2001 | Kurz et al. | |
| 6,309,367 B1 | 10/2001 | Boock | |
| 6,375,668 B1 | 4/2002 | Gifford et al. | |
| 6,397,850 B1 | 6/2002 | Scheldrup et al. | |
| 6,464,699 B1 | 10/2002 | Swanson | |
| 6,478,773 B1 | 11/2002 | Gandhi et al. | |
| 6,585,767 B1 | 7/2003 | Holley et al. | |
| 6,589,236 B2 | 7/2003 | Wheelock et al. | |
| 6,589,251 B2 | 7/2003 | Yee et al. | |
| 6,602,261 B2 | 8/2003 | Greene et al. | |
| 6,605,101 B1 | 8/2003 | Schaefer et al. | |
| 6,656,351 B2 | 12/2003 | Boyle | |
| 6,793,673 B2 * | 9/2004 | Kowalsky | A61F 2/2451 623/2.36 |
| 6,797,001 B2 | 9/2004 | Mathis et al. | |
| 6,849,081 B2 | 2/2005 | Sepetka et al. | |
| 6,878,384 B2 | 4/2005 | Cruise et al. | |
| 6,964,683 B2 * | 11/2005 | Kowalsky | A61F 2/2451 623/2.36 |
| 6,966,892 B2 * | 11/2005 | Gandhi | A61B 17/1214 604/114 |
| 6,994,689 B1 | 2/2006 | Zadno-Azizi et al. | |
| 7,018,394 B2 | 3/2006 | Diaz et al. | |
| 7,022,133 B2 | 4/2006 | Yee et al. | |
| 7,201,768 B2 | 4/2007 | Diaz et al. | |
| 7,229,461 B2 | 6/2007 | Chin et al. | |
| 7,294,146 B2 | 11/2007 | Chew et al. | |
| 7,331,973 B2 | 2/2008 | Gesswein et al. | |
| 7,344,558 B2 | 3/2008 | Lorenzo et al. | |
| 7,364,588 B2 * | 4/2008 | Mathis | A61F 2/2451 623/2.37 |
| 7,367,987 B2 | 5/2008 | Balgobin et al. | |
| 7,371,252 B2 | 5/2008 | Balgobin et al. | |
| 7,377,932 B2 | 5/2008 | Mitelberg et al. | |
| 7,419,501 B2 | 9/2008 | Shiu et al. | |
| 7,473,266 B2 | 1/2009 | Glaser | |
| 7,591,829 B2 | 9/2009 | Gibson et al. | |
| 7,601,160 B2 | 10/2009 | Richter | |
| 7,691,124 B2 | 4/2010 | Balgobin | |
| 7,708,755 B2 | 5/2010 | Davis et al. | |
| 7,722,636 B2 | 5/2010 | Farnan | |
| 7,722,637 B2 | 5/2010 | Barry et al. | |
| 7,811,305 B2 | 10/2010 | Balgobin et al. | |
| 7,901,444 B2 | 3/2011 | Slazas | |
| 7,918,872 B2 | 4/2011 | Mitelberg et al. | |
| 7,942,894 B2 | 5/2011 | West | |
| RE42,625 E | 8/2011 | Guglielmi | |
| 8,007,509 B2 | 8/2011 | Buiser et al. | |
| RE42,758 E | 9/2011 | Ken et al. | |
| 8,016,852 B2 | 9/2011 | Ho et al. | |
| 8,029,466 B2 | 10/2011 | Wilson et al. | |
| 8,034,073 B2 | 10/2011 | Davis et al. | |
| 8,043,326 B2 | 10/2011 | Hancock et al. | |
| 8,062,325 B2 | 11/2011 | Mitelberg et al. | |
| 8,100,918 B2 | 1/2012 | Gandhi et al. | |
| 8,142,456 B2 | 3/2012 | Rosqueta et al. | |
| 8,157,823 B2 | 4/2012 | Aronson et al. | |
| 8,333,796 B2 | 12/2012 | Tompkins et al. | |
| 8,425,541 B2 | 4/2013 | Masters et al. | |
| 8,470,013 B2 | 6/2013 | Duggal et al. | |
| 8,636,764 B2 | 1/2014 | Miles et al. | |
| 8,715,317 B1 | 5/2014 | Janardhan et al. | |
| 8,747,597 B2 | 6/2014 | Rosqueta et al. | |
| 8,777,974 B2 | 7/2014 | Amplatz et al. | |
| 8,777,978 B2 * | 7/2014 | Strauss | A61F 2/01 606/200 |
| 8,834,515 B2 | 9/2014 | Win et al. | |
| 8,906,057 B2 | 12/2014 | Connor et al. | |
| 8,926,650 B2 | 1/2015 | Que et al. | |
| 8,956,381 B2 | 2/2015 | Que et al. | |
| 9,095,342 B2 | 8/2015 | Becking et al. | |
| 9,119,948 B2 | 9/2015 | Lee et al. | |
| 9,211,202 B2 | 12/2015 | Strother et al. | |
| 9,339,275 B2 * | 5/2016 | Trommeter | A61B 17/12145 |
| 9,393,022 B2 | 7/2016 | Becking et al. | |
| 9,486,224 B2 | 11/2016 | Riina et al. | |
| 9,687,246 B2 | 6/2017 | Torp | |
| 9,814,562 B2 | 11/2017 | Halden et al. | |
| 9,833,309 B2 | 12/2017 | Levi et al. | |
| 9,844,380 B2 | 12/2017 | Furey | |
| 9,907,684 B2 | 3/2018 | Connor et al. | |
| 9,962,146 B2 | 5/2018 | Hebert et al. | |
| 10,028,745 B2 | 7/2018 | Morsi | |
| 10,064,628 B2 | 9/2018 | Edmiston et al. | |
| 10,076,335 B2 | 9/2018 | Zaver et al. | |
| 10,076,336 B2 | 9/2018 | Kleshinski et al. | |
| 10,206,685 B2 * | 2/2019 | Trommeter | A61B 17/12022 |
| 10,743,882 B2 * | 8/2020 | Kleshinski | A61B 17/12172 |
| 2001/0000797 A1 | 5/2001 | Mazzocchi | |
| 2001/0001835 A1 | 5/2001 | Greene et al. | |

(56) References Cited

U.S. PATENT DOCUMENTS

| | | |
|---|---|---|
| 2001/0002438 A1 | 5/2001 | Sepetka et al. |
| 2001/0037141 A1 | 11/2001 | Yee et al. |
| 2002/0010481 A1 | 1/2002 | Jayaraman |
| 2002/0072712 A1 | 6/2002 | Nool et al. |
| 2002/0116024 A1 | 8/2002 | Goldberg et al. |
| 2002/0143348 A1 | 10/2002 | Wallace et al. |
| 2003/0014073 A1 | 1/2003 | Bashiri et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0045901 A1 | 3/2003 | Opolski |
| 2003/0171770 A1 | 9/2003 | Kusleika et al. |
| 2003/0199966 A1 | 10/2003 | Shiu et al. |
| 2004/0002731 A1 | 1/2004 | Aganon et al. |
| 2004/0002733 A1 | 1/2004 | Teoh |
| 2004/0034363 A1 | 2/2004 | Wilson et al. |
| 2004/0087964 A1 | 5/2004 | Diaz et al. |
| 2004/0106946 A1 | 6/2004 | Ferrera et al. |
| 2004/0181256 A1 | 9/2004 | Glaser |
| 2004/0243228 A1 | 12/2004 | Kowalsky et al. |
| 2005/0021023 A1 | 1/2005 | Guglielmi et al. |
| 2005/0222605 A1 | 10/2005 | Greenhalgh et al. |
| 2005/0267511 A1 | 12/2005 | Marks et al. |
| 2006/0025792 A1 | 2/2006 | Gibson et al. |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116714 A1 | 6/2006 | Sepetka et al. |
| 2006/0155323 A1 | 7/2006 | Porter et al. |
| 2006/0200234 A1 | 9/2006 | Hines |
| 2006/0206199 A1 | 9/2006 | Churchwell et al. |
| 2006/0271097 A1 | 11/2006 | Ramzipoor et al. |
| 2006/0271099 A1 | 11/2006 | Marks et al. |
| 2006/0276823 A1 | 12/2006 | Mitelberg et al. |
| 2006/0276824 A1 | 12/2006 | Mitelberg et al. |
| 2006/0278680 A1 | 12/2006 | Viola et al. |
| 2007/0100426 A1 | 5/2007 | Rudakov et al. |
| 2007/0135826 A1 | 6/2007 | Zaver et al. |
| 2007/0173757 A1 | 7/2007 | Levine et al. |
| 2007/0175536 A1 | 8/2007 | Monetti et al. |
| 2007/0179520 A1 | 8/2007 | West |
| 2007/0185524 A1 | 8/2007 | Diaz et al. |
| 2007/0191924 A1 | 8/2007 | Rudakov |
| 2007/0221230 A1 | 9/2007 | Thompson et al. |
| 2007/0239192 A1 | 10/2007 | Litzenberg et al. |
| 2007/0239193 A1 | 10/2007 | Simon et al. |
| 2007/0265656 A1 | 11/2007 | Amplatz et al. |
| 2007/0267281 A1 | 11/2007 | Smith |
| 2007/0270936 A1 | 11/2007 | Andreas et al. |
| 2007/0282373 A1 | 12/2007 | Ashby et al. |
| 2008/0045997 A1 | 2/2008 | Balgobin et al. |
| 2008/0097462 A1 | 4/2008 | Mitelberg et al. |
| 2008/0119886 A1 | 5/2008 | Greenhalgh et al. |
| 2008/0119887 A1 | 5/2008 | Que et al. |
| 2008/0228215 A1 | 9/2008 | Strauss et al. |
| 2008/0243106 A1 | 10/2008 | Coe et al. |
| 2008/0255542 A1 | 10/2008 | Nimgaard et al. |
| 2008/0281350 A1 | 11/2008 | Sepetka et al. |
| 2008/0300616 A1 | 12/2008 | Que et al. |
| 2008/0306504 A1 | 12/2008 | Win et al. |
| 2009/0012554 A1 | 1/2009 | Makower et al. |
| 2009/0018653 A1 | 1/2009 | Bashiri et al. |
| 2009/0024154 A1 | 1/2009 | Williams et al. |
| 2009/0062812 A1 | 3/2009 | Fitz et al. |
| 2009/0076623 A1 | 3/2009 | Mathis et al. |
| 2009/0088832 A1 | 4/2009 | Chew et al. |
| 2009/0138036 A1 | 5/2009 | Nardone et al. |
| 2009/0163780 A1 | 6/2009 | Tieu |
| 2009/0163986 A1 | 6/2009 | Tieu et al. |
| 2009/0177261 A1 | 7/2009 | Teoh et al. |
| 2009/0182268 A1 | 7/2009 | Thielen et al. |
| 2009/0254169 A1 | 10/2009 | Spenser et al. |
| 2009/0270877 A1 | 10/2009 | Johnson et al. |
| 2009/0275974 A1 | 11/2009 | Marchand et al. |
| 2009/0287291 A1 | 11/2009 | Becking et al. |
| 2009/0312748 A1 | 12/2009 | Johnson et al. |
| 2010/0004673 A1 | 1/2010 | Denison et al. |
| 2010/0030200 A1 | 2/2010 | Strauss et al. |
| 2010/0094395 A1 | 4/2010 | Kellett |
| 2010/0144895 A1 | 6/2010 | Porter |
| 2010/0152767 A1 | 6/2010 | Greenhalgh et al. |
| 2010/0174269 A1 | 7/2010 | Tompkins et al. |
| 2010/0234872 A1 | 9/2010 | Guo et al. |
| 2010/0256666 A1 | 10/2010 | Chen et al. |
| 2010/0268204 A1 | 10/2010 | Tieu et al. |
| 2010/0268251 A1 | 10/2010 | Chen et al. |
| 2010/0268252 A1 | 10/2010 | Chen et al. |
| 2011/0022003 A1 | 1/2011 | Tekulve |
| 2011/0106098 A1 | 5/2011 | Williams |
| 2011/0106128 A1 | 5/2011 | Chen |
| 2011/0118772 A1 | 5/2011 | Chen et al. |
| 2011/0118776 A1 | 5/2011 | Chen et al. |
| 2011/0137405 A1 | 6/2011 | Wilson et al. |
| 2011/0172700 A1 | 7/2011 | Bose et al. |
| 2011/0202085 A1 | 8/2011 | Loganathan et al. |
| 2011/0208227 A1 | 8/2011 | Becking |
| 2011/0265943 A1 | 11/2011 | Rosqueta et al. |
| 2011/0282380 A1 | 11/2011 | Davis et al. |
| 2011/0301686 A1 | 12/2011 | Bowman et al. |
| 2011/0313447 A1 | 12/2011 | Strauss et al. |
| 2011/0319926 A1 | 12/2011 | Becking et al. |
| 2012/0041470 A1 | 2/2012 | Shrivastava et al. |
| 2012/0041472 A1 | 2/2012 | Tan et al. |
| 2012/0046687 A1 | 2/2012 | Trommeter et al. |
| 2012/0065720 A1 | 3/2012 | Strauss et al. |
| 2012/0101510 A1 | 4/2012 | Lenker et al. |
| 2012/0226305 A1 | 9/2012 | Strauss et al. |
| 2012/0239077 A1 | 9/2012 | Zaver et al. |
| 2012/0283758 A1 | 11/2012 | Miller et al. |
| 2012/0316598 A1 | 12/2012 | Becking et al. |
| 2012/0316632 A1 | 12/2012 | Gao |
| 2012/0330347 A1 | 12/2012 | Becking et al. |
| 2013/0066360 A1 | 3/2013 | Becking et al. |
| 2013/0085520 A1 | 4/2013 | Liang et al. |
| 2013/0085521 A1 | 4/2013 | Lim |
| 2013/0085522 A1 | 4/2013 | Becking et al. |
| 2013/0123830 A1 | 5/2013 | Becking et al. |
| 2013/0138136 A1 | 5/2013 | Beckham et al. |
| 2013/0211495 A1 | 8/2013 | Halden et al. |
| 2013/0274866 A1 | 10/2013 | Cox et al. |
| 2014/0012307 A1 | 1/2014 | Franano et al. |
| 2014/0058420 A1 | 2/2014 | Hannes et al. |
| 2014/0081314 A1 | 3/2014 | Zaver et al. |
| 2014/0316012 A1 | 10/2014 | Freyman et al. |
| 2014/0371734 A1 | 12/2014 | Truckai |
| 2015/0216684 A1 | 8/2015 | Enzmann et al. |
| 2015/0250628 A1 | 9/2015 | Monstadt et al. |
| 2015/0313737 A1 | 11/2015 | Tippett et al. |
| 2015/0327843 A1 | 11/2015 | Garrison |
| 2016/0008003 A1 | 1/2016 | Kleshinski et al. |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0278784 A1 | 9/2016 | Edmiston et al. |
| 2017/0150971 A1 | 6/2017 | Hines |
| 2017/0156903 A1 | 6/2017 | Shobayashi |
| 2017/0189035 A1 | 7/2017 | Porter |
| 2017/0266023 A1 | 9/2017 | Thomas |
| 2017/0340333 A1 | 11/2017 | Badruddin et al. |
| 2017/0367708 A1 | 12/2017 | Mayer et al. |
| 2018/0049859 A1 | 2/2018 | Stoppenhagen et al. |
| 2018/0125686 A1 | 5/2018 | Lu |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2018/0368854 A1 | 12/2018 | Kleshinski et al. |
| 2018/0368855 A1 | 12/2018 | Edmiston et al. |

(56) References Cited

U.S. PATENT DOCUMENTS

| | | |
|---|---|---|
| 2019/0053811 A1 | 2/2019 | Garza et al. |
| 2020/0337709 A1* | 10/2020 | Kleshinski ....... A61B 17/12031 |

FOREIGN PATENT DOCUMENTS

| | | |
|---|---|---|
| CN | 1668250 A | 9/2005 |
| CN | 101234034 A | 8/2008 |
| CN | 101835430 A | 9/2010 |
| CN | 102119004 A | 7/2011 |
| CN | 102149336 A | 8/2011 |
| EP | 0029236 A1 | 5/1981 |
| EP | 0621150 A2 | 10/1994 |
| EP | 0717969 A2 | 6/1996 |
| EP | 0832607 A1 | 4/1998 |
| EP | 0853955 A1 | 7/1998 |
| EP | 1400208 A1 | 3/2004 |
| EP | 0996372 B1 | 9/2004 |
| EP | 1487526 A1 | 12/2004 |
| EP | 1738698 A2 | 1/2007 |
| JP | 2004073874 A | 3/2004 |
| JP | 2004267749 A | 9/2004 |
| JP | 2006051349 A | 2/2006 |
| JP | 2009533202 A | 9/2009 |
| WO | 9221400 A1 | 12/1992 |
| WO | 9311719 A1 | 6/1993 |
| WO | 9406502 A2 | 3/1994 |
| WO | 9834546 A1 | 8/1998 |
| WO | 9858590 A1 | 12/1998 |
| WO | 02054943 A2 | 7/2002 |
| WO | 2004087006 A2 | 10/2004 |
| WO | 2007070797 A2 | 6/2007 |
| WO | 2007121405 A2 | 10/2007 |
| WO | 2008112435 A2 | 9/2008 |
| WO | 2008127525 A1 | 10/2008 |
| WO | 2010009019 A1 | 1/2010 |
| WO | 2010117883 A1 | 10/2010 |
| WO | 2010123821 A1 | 10/2010 |
| WO | 2011066962 A1 | 6/2011 |
| WO | 2017074411 A1 | 5/2017 |
| WO | 2018051187 A1 | 3/2018 |

OTHER PUBLICATIONS

Ronnen, et al., "Amplatzer Vascular Plug Case Study, Closure of Arteriovenous Fistula Between Deep Femoral Artery and Superficial Femoral Vein", AGA Medical Corporation, May 2007.

* cited by examiner

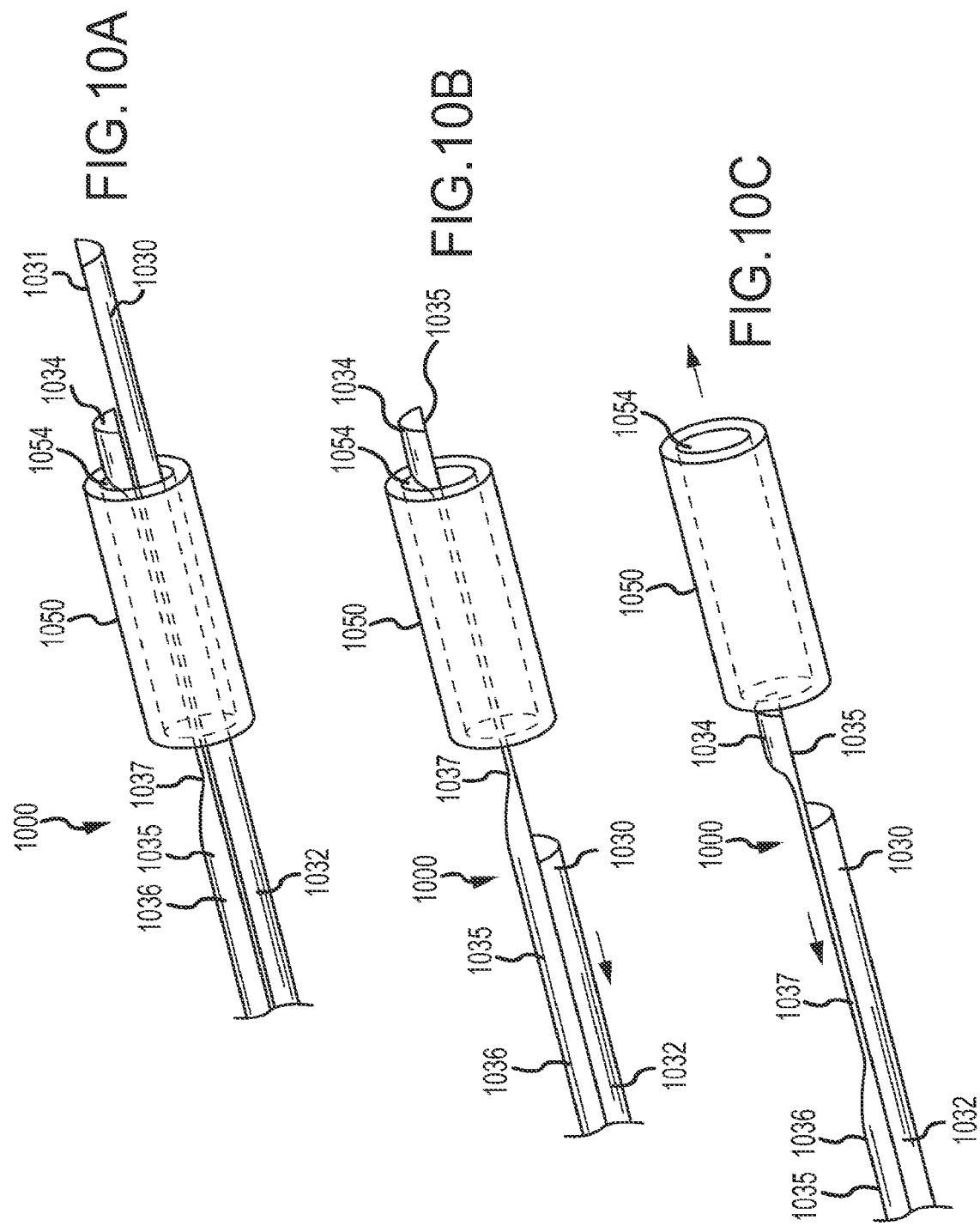

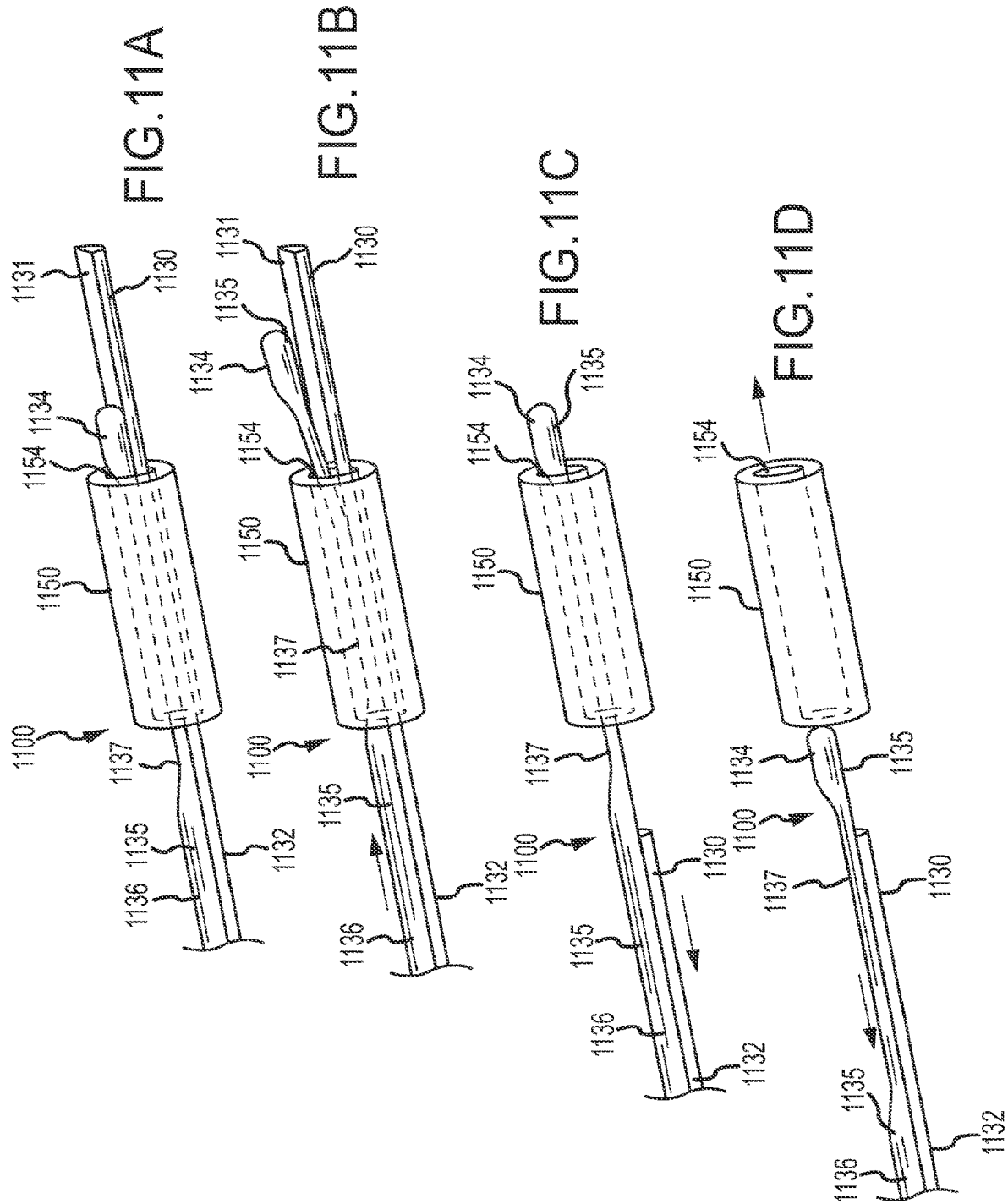

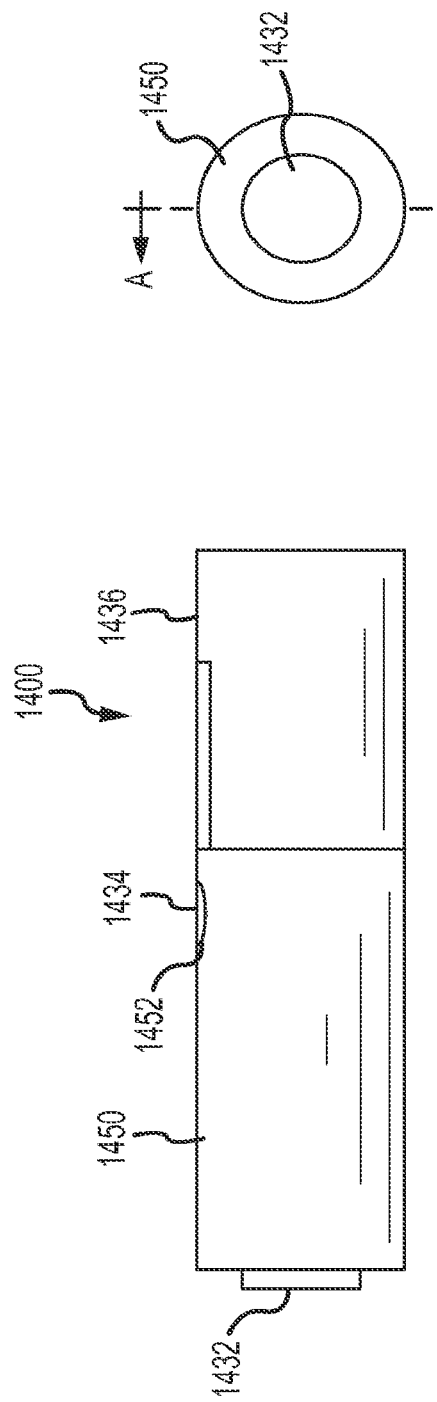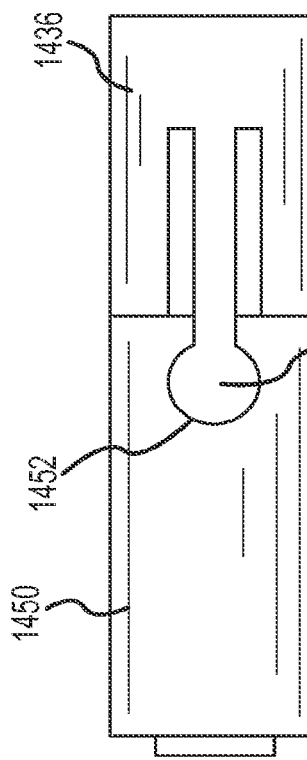

SECTION A-A

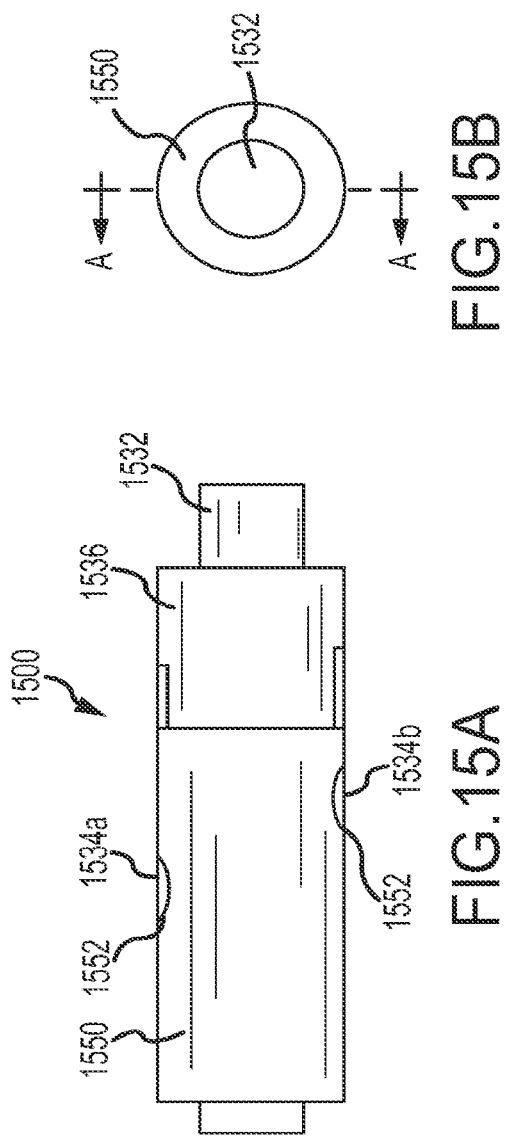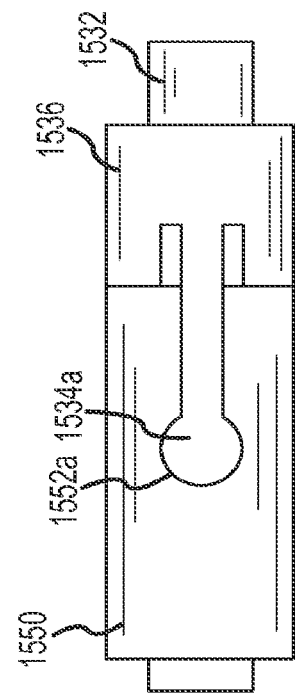

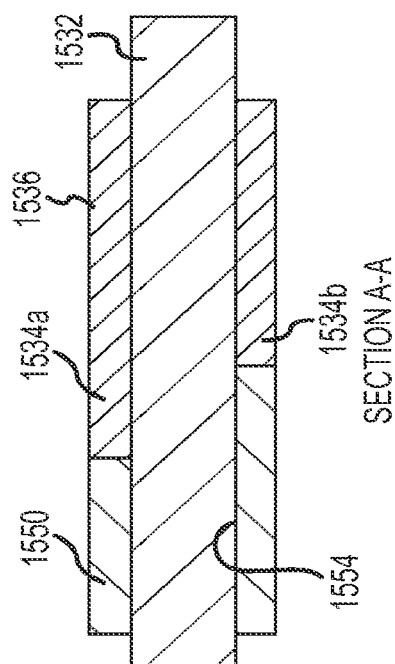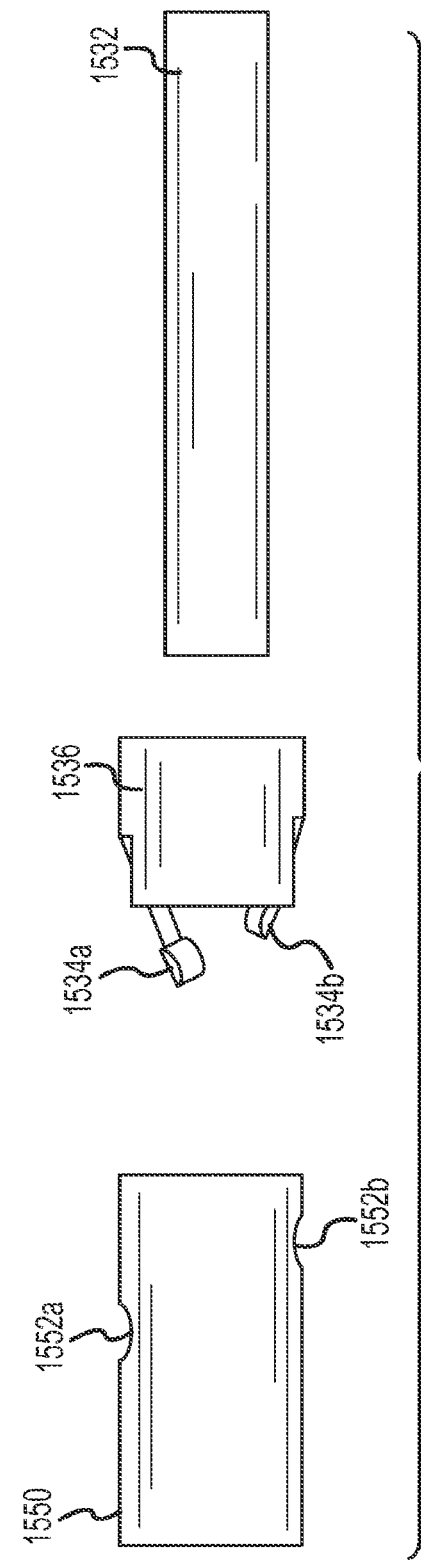

DELIVERY AND DETACHMENT MECHANISMS FOR VASCULAR IMPLANTS

RELATED APPLICATIONS

The present application is a continuation of U.S. patent application Ser. No. 16/103,448, entitled "Delivery and Detachment Mechanisms for Vascular Implants," filed Aug. 14, 2018, which is a continuation of U.S. patent application Ser. No. 14/776,815 entitled "Delivery and Detachment Mechanisms for Vascular Implants," filed on Sep. 15, 2015, now U.S. Pat. No. 10,076,336, issued Sep. 18, 2018, which claims the benefit of International Patent Application Serial No. PCT/US2014/029647 entitled "Implant Structures and Methods," filed on Mar. 14, 2014, which claims priority from U.S. Provisional Application No. 61/792,147, entitled "Implant Detachment Structures and Methods," filed Mar. 15, 2013, the entirety of each being hereby incorporated herein by reference.

FIELD

The subject technology relates to delivery and detachment mechanisms. In particular, the subject technology relates to delivery and detachment mechanisms for vascular implants.

BACKGROUND

Mainstream clinical practice in endovascular treatment of intracranial aneurysms has changed little since the introduction of vasooclusive coils. Certainly, improved catheters and other auxiliary devices (e.g., stents) have helped make coiling procedures safer and/or more effective.

Delivery systems of the subject technology provide accurate and reliable placement and delivery of endovascular treatment devices for treating vascular malformations, including aneurysms.

SUMMARY

The subject technology is illustrated, for example, according to various aspects described below.

According to some exemplary implementations, a vascular delivery system includes an implant having, at a proximal region, a hub defining a port having an inner cross-sectional dimension; an anchor wire having an anchor portion, distal to the port, with an anchor cross-sectional dimension; a control wire having an engagement portion, distal to the port and radially adjacent to the anchor portion, with an engagement cross-sectional dimension and being retractable proximally relative to the anchor portion; wherein the anchor portion is configured to remain distal to the port until the engagement portion is retracted proximally past the port; wherein the anchor wire is of a first material and the control wire is of the second material less flexible than the first material, such that the anchor portion is configured to deflect away from the engagement portion.

According to some exemplary implementations, the inner cross-sectional dimension can be less than the sum of the anchor cross-sectional dimension and the engagement cross-sectional dimension. The anchor wire can include a neck portion, proximal to the anchor portion, with a neck cross-sectional dimension less than the anchor cross-sectional dimension. The anchor wire can have a first longitudinally extending flat surface and the control wire has a second longitudinally extending flat surface, facing the first longitudinally extending flat surface.

According to some exemplary implementations, a method of delivering a vascular implant includes delivering, to a target location, an implant having, at a proximal region, a hub defining a port having an inner cross-sectional dimension, the hub being engaged by (i) an anchor wire through the port having an anchor portion, distal to the port, with an anchor cross-sectional dimension and (ii) a control wire through the port having an engagement portion, distal to the port and radially adjacent to the anchor portion, with an engagement cross-sectional dimension, wherein the anchor wire is of a first material and the control wire is of a second material, more flexible than the first material, such that the engagement portion is configured to deflect away from the anchor portion; retracting the control wire proximally past the port; and retracting the engagement portion proximally past the port.

According to some exemplary implementations, a vascular delivery system includes an implant having, at a proximal region, a hub defining a port having an inner cross-sectional dimension; a shaft having a collet, distal to the port, having a flared state with a flared cross-sectional dimension and a relaxed state with a relaxed cross-sectional dimension less than the flared cross-sectional dimension; a control wire extending through the collet and having an engagement portion, distal to at least a portion of the collet, with an engagement cross-sectional dimension greater than the relaxed cross-sectional dimension, and being retractable relative to the collet, wherein proximal retraction of the engagement portion against the collet causes the collet to transition from the relaxed state to the flared state; wherein the collet is configured to remain distal to the port while in the flared state.

The flared cross-sectional dimension can be greater than the inner cross-sectional dimension, and the relaxed cross-sectional dimension can be less than the inner cross-sectional dimension. The collet can include a plurality of fingers extending from a proximal section of the shaft. The collet can be biased to assume the relaxed state when unconstrained.

According to some exemplary implementations, a method of delivering a vascular implant includes delivering, to a target location, an implant having a hub at a proximal end of the implant, while (i) a shaft extends through a port of the hub, (ii) a collet of the shaft, in a flared state with a flared cross-sectional dimension greater than an inner cross-sectional dimension of the port, is distal to the port, (iii) a control wire extends through the collet, and (iv) an engagement portion of the control wire abuts the collet to hold the collet in the flared state; retracting the control wire distally until the collet transitions to a relaxed state with a relaxed cross-sectional dimension less than the inner cross-sectional dimension; retracting the shaft proximally past the port; and retracting the control wire proximally past the port.

According to some exemplary implementations, a vascular delivery system includes an implant having, at a proximal region, a hub defining a port having an inner cross-sectional dimension; a shaft having an interference section including a plurality of extensions, distal to the port, having an extended state with an extended cross-sectional dimension and a relaxed state with a relaxed cross-sectional dimension less than the flared cross-sectional dimension; a control wire extending through the shaft and having an engagement portion, radially adjacent to the interference section, and being retractable relative to the interference section, wherein proximal retraction of the engagement portion proximal to the interference section causes the interference section to transition from the extended state to the relaxed state;

wherein the interference section is configured to remain distal to the port while in the extended state.

The extended cross-sectional dimension can be greater than the inner cross-sectional dimension and the relaxed cross-sectional dimension can be less than the inner cross-sectional dimension. The extended cross-sectional dimension can be defined by a distance between protrusions of a pair of extensions, extending radially outward from a central axis of the system. The interference section can be biased to assume the relaxed state when unconstrained.

According to some exemplary implementations, a method of delivering a vascular implant includes delivering, to a target location, an implant having a hub at a proximal end of the implant, while (i) a shaft extends through a port of the hub, (ii) an interference section of the shaft, in an extended state with an extended cross-sectional dimension greater than an inner cross-sectional dimension of the port, is distal to the port, (iii) a control wire extends through the interference section to hold the interference section in the extended state; retracting the control wire proximally until the interference section transitions to a relaxed state with a relaxed cross-sectional dimension less than the inner cross-sectional dimension; retracting the shaft proximally past the port; and retracting the control wire proximally past the port.

According to some exemplary implementations, a vascular delivery system includes an implant having, at a proximal region, a hub defining a lumen, with a central axis, and a first keyhole extending radially through a wall of the hub; a shaft having a first appendage engaged within the first keyhole in a deflected state and entirely within the lumen in a relaxed state; a control wire having an engagement portion configured to extend within the lumen and be controllably retracted proximally relative to the first appendage; wherein the engagement portion is configured to deflect the first appendage into the deflected state while the engagement portion is radially adjacent to the first appendage; wherein the first appendage is configured to achieve the relaxed state when the engagement portion is retracted proximally past the first appendage.

The hub can be secured relative to the shaft when the first appendage is engaged within the first keyhole. The vascular delivery system can further include a second appendage of the shaft engaged within a second keyhole of the hub. The second appendage can be axially aligned with the first appendage. The second appendage can be axially offset relative to the first appendage.

According to some exemplary implementations, a method of delivering a vascular implant includes delivering, to a target location, an implant having a hub at a proximal end of the implant, while (i) an appendage of a shaft engages a keyhole extending radially through a wall of the hub in an extended state and (ii) a control wire extends through a lumen defined by the shaft and the hub to hold the appendage in the extended state; retracting the control wire proximally until the appendage transitions radially inwardly to a relaxed state out of the keyhole and entirely within the lumen; and retracting the shaft proximally away from the hub.

According to some exemplary implementations, a vascular delivery system includes an implant having, at a proximal region, a hub with a central axis, and a first keyhole extending radially into a wall of the hub; a shaft having a first appendage engaged within the first keyhole in a constrained state and radially away from the central axis and entirely out of the first keyhole in a relaxed state; a constraining collar configured to extend over the first appendage and about the hub and be controllably retracted proximally relative to the first appendage; wherein the constraining collar is configured to deflect the first appendage into the constrained state while the constraining collar is covering the first appendage; wherein the first appendage is configured to achieve the relaxed state when the constraining collar is retracted proximally past the first appendage.

The hub can be secured relative to the shaft when the first appendage is engaged within the first keyhole. The vascular delivery system can further include a second appendage of the shaft engaged within a second keyhole of the hub. The second appendage can be axially aligned with the first appendage. The second appendage can be axially offset relative to the first appendage.

According to some exemplary implementations, a method of delivering a vascular implant includes delivering, to a target location, an implant having a hub at a proximal end of the implant, while (i) an appendage of a shaft engages a keyhole extending radially through a wall of the hub in a constrained state and (ii) a constraining collar extends over the appendage and about the hub to hold the appendage in the constrained state; retracting the constraining collar proximally until the appendage transitions radially outwardly to a relaxed state out of the keyhole; and retracting the shaft proximally away from the hub.

Additional features and advantages of the subject technology will be set forth in the description below, and in part will be apparent from the description, or can be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 10A, 10B, and 10C show perspective side views of a vascular delivery system with half round wire profiles, in accordance with one or more exemplary implementations of the present disclosure.

FIGS. 11A, 11B, 11C, and 11D show perspective side views of a vascular delivery system with half round wire profiles, in accordance with one or more exemplary implementations of the present disclosure.

FIG. 14A shows a side view of a vascular delivery system with interlocking tubes, in accordance with one or more exemplary implementations of the present disclosure FIG. 14B shows a front view of a vascular delivery system with interlocking tubes, in accordance with one or more exemplary implementations of the present disclosure FIG. 14C shows a top view of a vascular delivery system with interlocking tubes, in accordance with one or more exemplary implementations of the present disclosure

FIG. 15A shows a side view of a vascular delivery system with interlocking tubes, in accordance with one or more exemplary implementations of the present disclosure FIG. 15B shows a front view of a vascular delivery system with interlocking tubes, in accordance with one or more exemplary implementations of the present disclosure FIG. 15C shows a top view of a vascular delivery system with interlocking tubes, in accordance with one or more exemplary implementations of the present disclosure FIG. 15D shows a side-sectional view of a vascular delivery system with interlocking tubes, in accordance with one or more exemplary implementations of the present disclosure FIG. 15E shows a side view of a vascular delivery system with interlocking tubes, in accordance with one or more exemplary implementations of the present disclosure.

DETAILED DESCRIPTION

In the following detailed description, specific details are set forth to provide an understanding of the subject technology. It will be apparent, however, to one ordinarily skilled in the art that the subject technology can be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect can apply to all configurations, or one or more configurations. An aspect can provide one or more examples of the disclosure. A phrase such as "an aspect" can refer to one or more aspects and vice versa. A phrase such as "an embodiment" does not imply that such embodiment is essential to the subject technology or that such embodiment applies to all configurations of the subject technology. A disclosure relating to an embodiment can apply to all embodiments, or one or more embodiments. An embodiment can provide one or more examples of the disclosure. A phrase such "an embodiment" can refer to one or more embodiments and vice versa. A phrase such as "a configuration" does not imply that such configuration is essential to the subject technology or that such configuration applies to all configurations of the subject technology. A disclosure relating to a configuration can apply to all configurations, or one or more configurations. A configuration can provide one or more examples of the disclosure. A phrase such as "a configuration" can refer to one or more configurations and vice versa.

Figure 1:
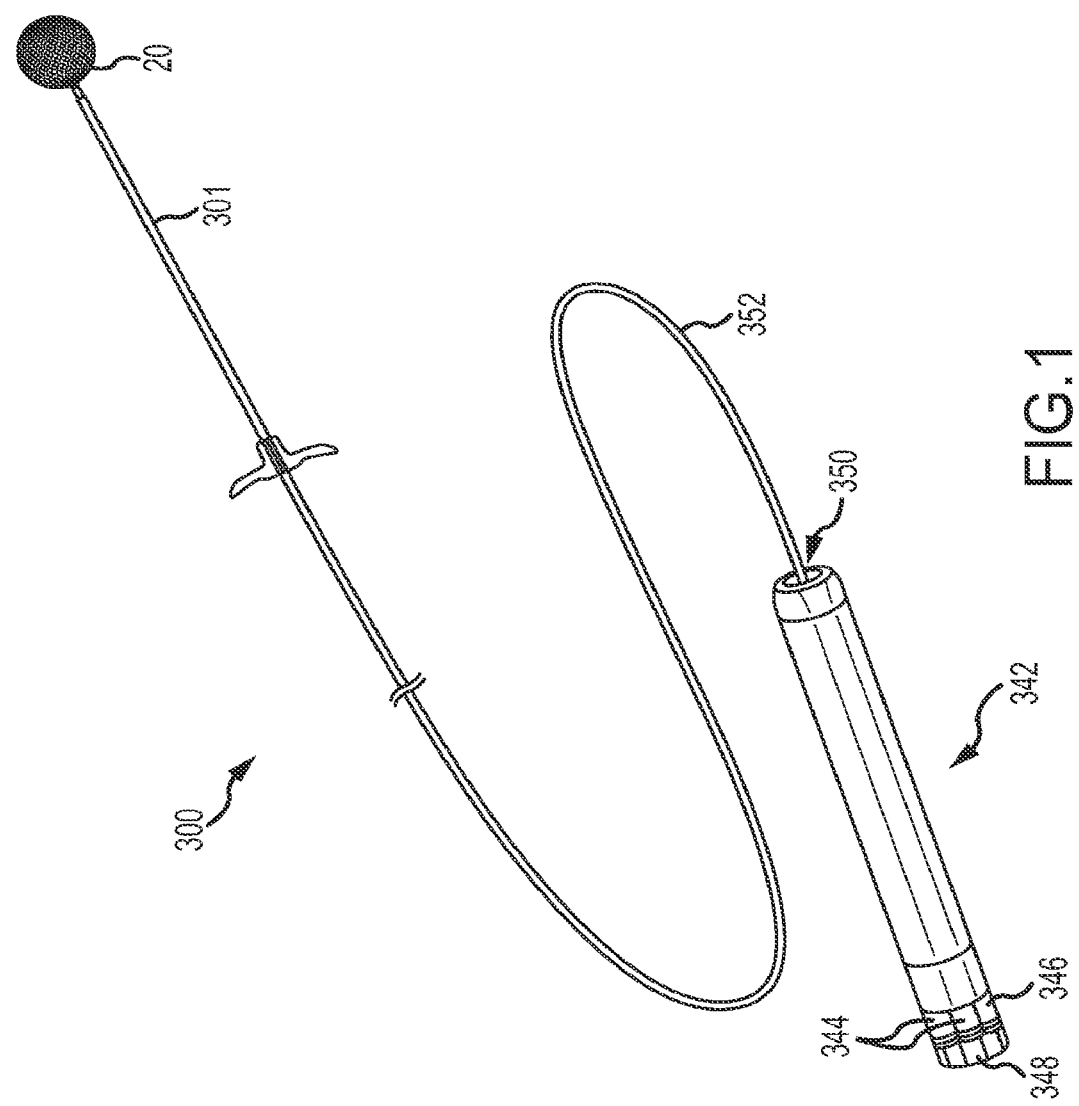
FIG. 1 shows a perspective view providing an overview of a treatment system, in accordance with one or more exemplary implementations of the present disclosure.

According to some exemplary implementations, FIG. 1 presents an overview of a treatment system 300 including an implant 20 and a handle 342. Either or both of these can be constructed according to the teachings herein. The handle 342 shown includes knobs connected to detachment mechanisms (e.g., wires) engaging to the implant 20. Two knobs 344 are connected to control wires (not shown), and the last knob 346 to an anchor wire (not shown). A removable locking cap 348 can be included in the handle design as well as a strain relief section 350. The catheter/pusher shaft 301 can include a simple extrusion (e.g., PTFE, FEP, PEEK, etc.) or can be constructed using conventional catheter construction techniques and include a liner, braid support and outer jacket (not shown). A loading sheath 352 is typically provided over the shaft of a pusher 301.

Figure 3:
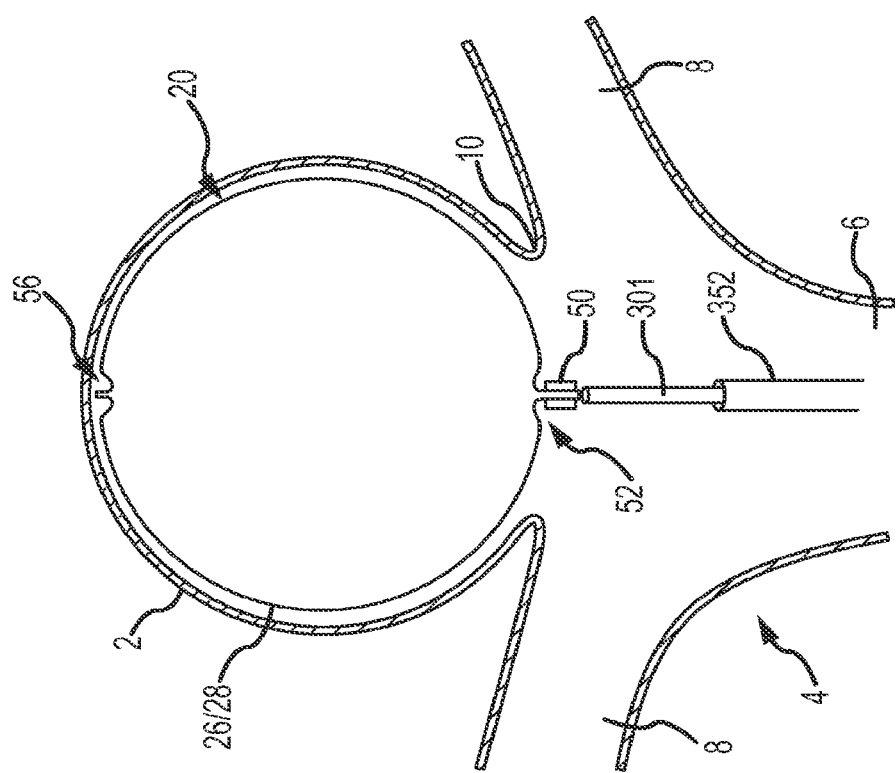
FIG. 3 shows a side-sectional view of a braid ball implant deployed within a bifurcation aneurysm, in accordance with one or more exemplary implementations of the present disclosure.
Figure 2:
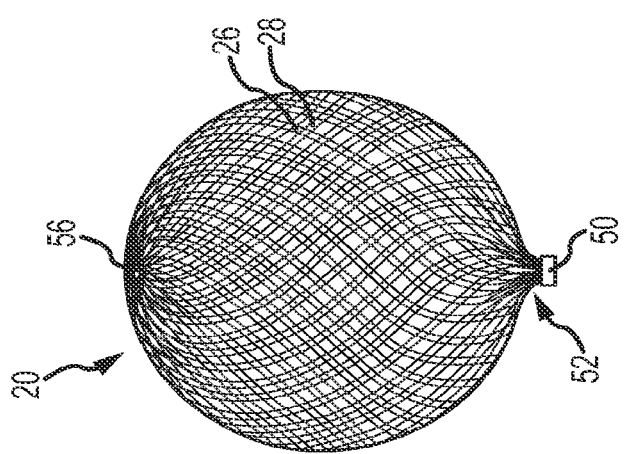
FIG. 2 shows a perspective side view of a braid ball, in accordance with one or more exemplary implementations of the present disclosure.

According to some exemplary implementations, as shown in FIGS. 2 and 3, an implant 20 delivered by the system 300 can be a braid ball. The braid ball 20 can be formed from tubular braid stock including a resilient material, such as Nitinol, that defines an open volume (generally round, spherical, ovular, heart-shaped, etc.) in an uncompressed/unconstrained state. The size of the implant can be selected to fill an aneurysm 2, so the proximal end 52 of the device helps direct blood flow along the surface of the braid from which it is constructed to the branch vessels 8. A distal end 56 of the ball is dome-shaped. The braid ball 20 can include a single layer or two layers 26, 28 (inner and outer layer, respectively) construction at least where impacted by flow at the neck 10 of the aneurysm 2. As shown, one or more turns of a coil (e.g., Pt wire) or a band (not shown) can provide a distal radiopaque feature to mark the location of the implant 20. Some exemplary implants that can be used in conjunction with the systems described herein are disclosed at U.S. Pub. No. 2013/0123830, published on May 16, 2013, the entirety of which is incorporated herein by reference.

According to some exemplary implementations, the implant 20 can include a hub 50 at a proximal end 52 thereof. The hub 50 can be fixedly attached to the remainder of the implant 20. For example, the hub 50 can grasp braided filaments of the layers 26, 28 of the implant 20. The hub 50 can provide a lumen 54 for receiving engagement and release mechanisms of a delivery system.

According to some exemplary implementations, the implant 20 can be set within an aneurysm sac 2 at a vascular bifurcation 4, formed by trunk vessel 8 and efferent vessels 8. The implant 20 can be delivered by access through the trunk vessel 8 (e.g., the basilar artery), preferably through a commercially available microcatheter with a delivery system as detailed below. To deliver the implant 20, the pusher sleeve 301 is positioned such that the implant 20 can be delivered at least partially into the aneurysm sac 2. After final positioning is achieved as shown in FIG. 3, engagement members are released from the implant 20 (e.g., from a hub 50 of the implant 20), as discussed further herein. Finally, the pusher sleeve 301 is withdrawn into the delivery catheter 352.

While the implant 20 can be a braid ball as illustrated herein, the implant 20 can have any other form or structure, according to various embodiments. For example, the implant 20 can be a vasoocclusive coil, a cylindrical, tube-like stent, or a filter. Other types of implants are generally known. The subject technology can be applied to any such implant for delivery and detachment thereof. For example, a given implant can include a hub 50 for engagement and release by a delivery system, as disclosed further herein.

Figure 5:
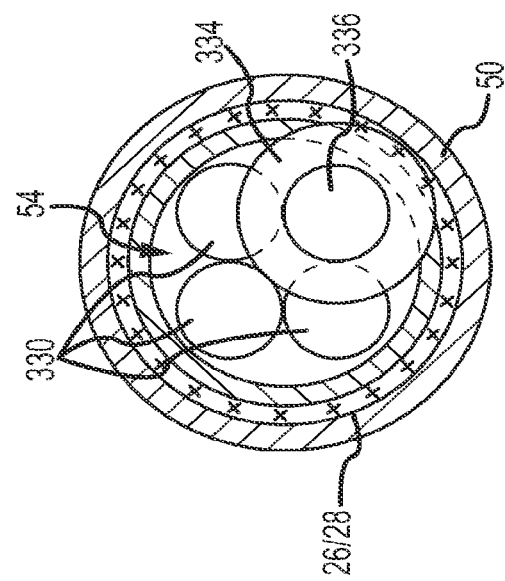
FIG. 5 shows an end view from within the implant of the system shown in FIG. 4, in accordance with one or more exemplary implementations of the present disclosure.
Figure 4:
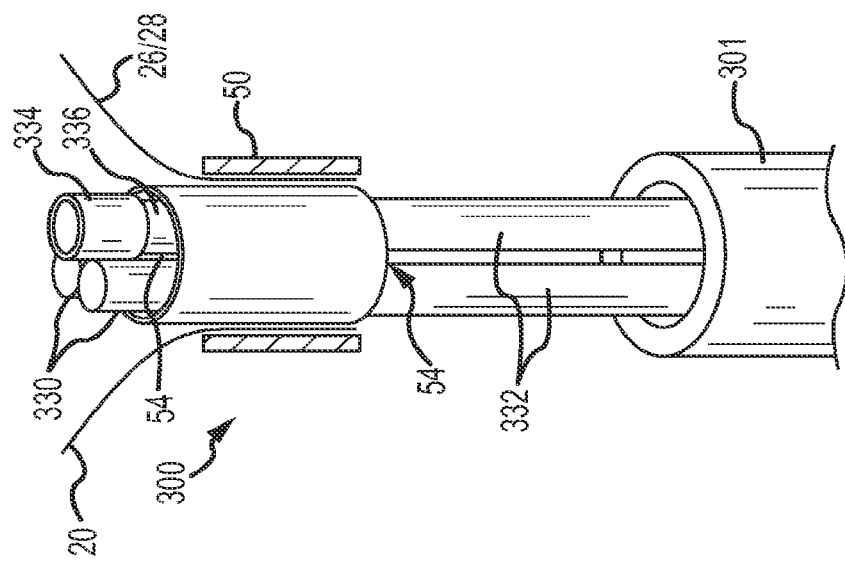
FIG. 4 shows a partial side-sectional view of a distal end of a delivery system, in accordance with one or more exemplary implementations of the present disclosure.

An exemplary detachable delivery system 300 is illustrated in FIGS. 4 and 5. According to some exemplary implementations, one or more control wires 332 and an anchor wire 336 extend partially or entirely through the lumen 54 of the hub 50 of the implant 20. The anchor wire 336 can include a head 334 having an enlarged cross-sectional dimension (e.g. diameter) relative to either or both of a distal portion 330 of the control wires 332 or a proximal portion of the anchor wire 336. The head 334 can be at a distal or distalmost portion of the anchor wire 336. Until one or more of the control wires 332 are removed from the lumen 54, the head 334 mounted on the anchor wire 336 is unable to pass through the lumen 54. The control wires 332 can extend to or past the anchor wire head 334.

Figure 6A:
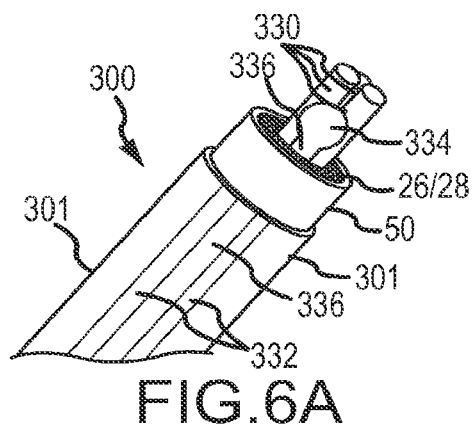
FIGS. 6A, 6B, 6C, 6D, 6E, and 6F show partial perspective views of implant detachment with a system, in accordance with one or more exemplary implementations of the present disclosure.
Figure 6D:
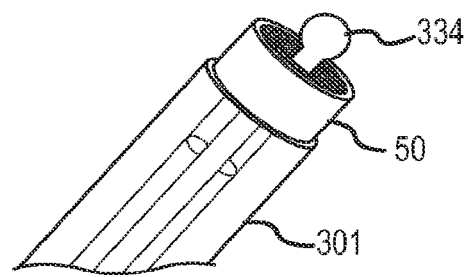
Figure 6B:
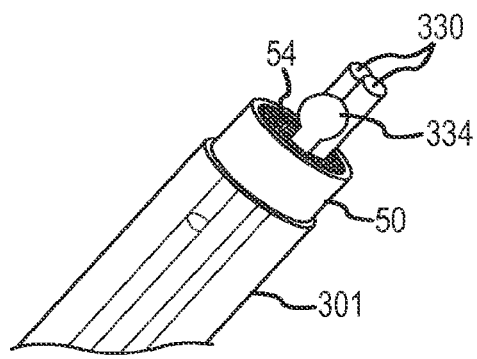
Figure 6E:
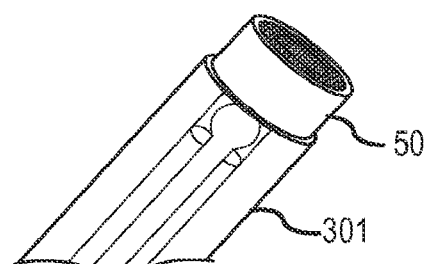
Figure 6C:
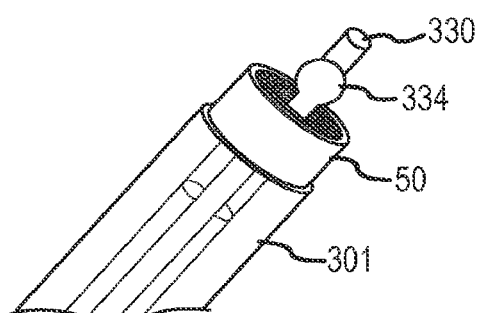
Figure 6F:
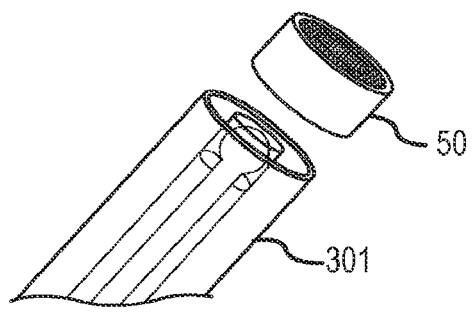

FIGS. 6A-6F illustrate operation of the delivery system 300 in use. The distal end of the detachment system is shown with the hub 50 of an implant 20. FIG. 6A shows the pusher 301 interlock engaged. FIGS. 6B-6D illustrate sequential withdrawal of the control wires 332. Because the wires are pulled straight out and only position the anchor wire head 334 to ensure interference minimal effort is required. EPTFE coating over at least the control wires 332 can be provided to facilitate removal. Anchor wire 336 can also be individually withdrawn as shown in FIG. 6E. However, it can instead by withdrawn with the detachment system sleeve 301. It is to be recognized that the control wires 332 need not be pulled one at a time, but rather can be actuated together. Complete implant (e.g., hub 50) separation is illustrated in FIG. 6F.

Figure 7:
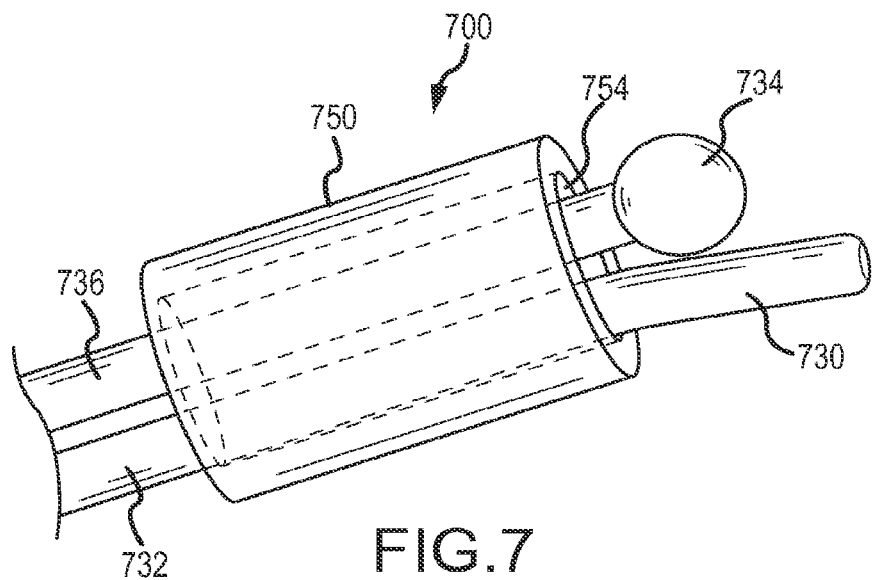
FIGS. 7 and 8 show a perspective side view of a vascular delivery system, in accordance with one or more exemplary implementations of the present disclosure.

According to some exemplary implementations, as shown in FIG. 7, a vascular delivery system 700 can include an implant hub 750 defining a port 754 having an inner cross-sectional dimension. An anchor wire 736 can extend through the port 754 such that an enlarged anchor portion 734 is positioned distal to the port 754 and the hub 750. The enlarged anchor portion 734 has an anchor cross-sectional dimension that is greater than a cross-sectional dimension of a proximal portion of the anchor wire. One or more control wires 732 can extend through the port 754 such that an engagement portion 730, at a distal or distalmost portion of each control wire 732, is positioned distal to the port 754 and the hub 750. The distal end 730 has an engagement cross-sectional dimension. The engagement portion 730 is retractable proximally relative to the anchor portion 734. The anchor portion 734 is configured to remain distal to the port 754 until the engagement portion 730 is retracted proximally past the port 754. According to some exemplary implementations, the inner cross-sectional dimension of the port 754 is less than the sum of the anchor cross-sectional dimension of the anchor portion 734 and the engagement cross-sectional dimension of the engagement portion 730.

According to some exemplary implementations, the anchor wire 736 is of a first material and the control wire 732 is of a second material, more flexible than the first material, such that the engagement portion 730 is configured to deflect away from the anchor portion 734 and a longitudinal axis of the system 700 at a region distal to the hub 750, while the anchor portion 734 maintains an alignment with the longitudinal axis. An exemplary delivery system 700 can include a super-elastic nitinol control wire 732 and a rigid stainless steel anchor wire 736.

Figure 8:
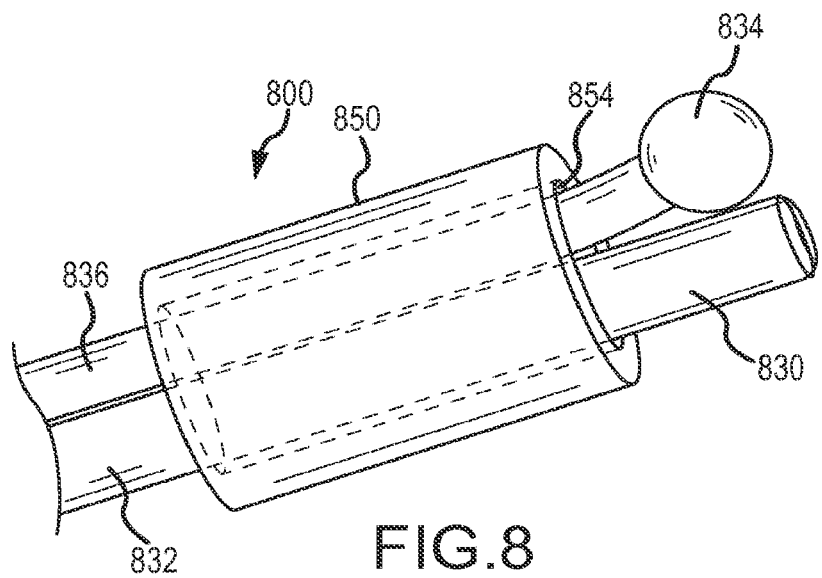

According to some exemplary implementations, as shown in FIG. 8, a vascular delivery system 800 can include an implant hub 850 defining a port 854 having an inner cross-sectional dimension. An anchor wire 836 can extend through the port 854 such that an enlarged anchor portion 834 is positioned distal to the port 854 and the hub 850. The enlarged anchor portion 834 has an anchor cross-sectional dimension that is greater than a cross-sectional dimension of a proximal portion of the anchor wire. One or more control wires 832 can extend through the port 854 such that an engagement portion 830, at a distal or distalmost portion of each control wire 832, is positioned distal to the port 854 and the hub 850. The distal end 830 has an engagement cross-sectional dimension. The engagement portion 830 is retractable proximally relative to the anchor portion 834. The anchor portion 834 is configured to remain distal to the port 854 until the engagement portion 830 is retracted proximally past the port 854. According to some exemplary implementations, the inner cross-sectional dimension of the port 854 is less than the sum of the anchor cross-sectional dimension of the anchor portion 834 and the engagement cross-sectional dimension of the engagement portion 830.

According to some exemplary implementations, the anchor wire 836 is of a first material and the control wire 832 is of a second material less flexible than the first material, such that the anchor portion 834 is configured to deflect away from the engagement portion 830 and a longitudinal axis of the system 800 at a region distal to the hub 850, while the control wire 832 maintains an alignment with the longitudinal axis. An exemplary delivery system 800 can include a super-elastic nitinol anchor wire 836 and a rigid stainless steel control wire 832.

The provision of a nitinol anchor wire 836 allows for a smaller cross section of the anchor wire 836 in the implant hub while providing a super-elastic recovery of the anchor wire 836 at the anchor portion 834 during detachment for easy separation from the implant (e.g., the hub 850). Stainless steel has a higher modulus of elasticity than nitinol. Using stainless steel for the control wire 832 provides greater stiffness to the control wire 832 while simultaneously reducing its elongation during detachment of the implant. A relatively rigid control wire 832 is less likely to bend over the edge of the port 854 of the hub 850, thereby decreasing friction and reducing stretching and elongation of the control wire 832 during detachment.

Geometry of the nitinol anchor wire 836 can take various forms. The tip that creates an interference fit at the distal end of the inner hub 850 can be formed as a ball by welding techniques, or can be shaped to a variety of geometries by profile grinding techniques. The shaft leading to the tip can also be ground or electrochemically machined to a smaller cross section, or taper through the length of inner hub, or beyond, to reduce frictional forces within the hub and reduce bending stiffness at the distal end of the delivery system.

Figure 9:
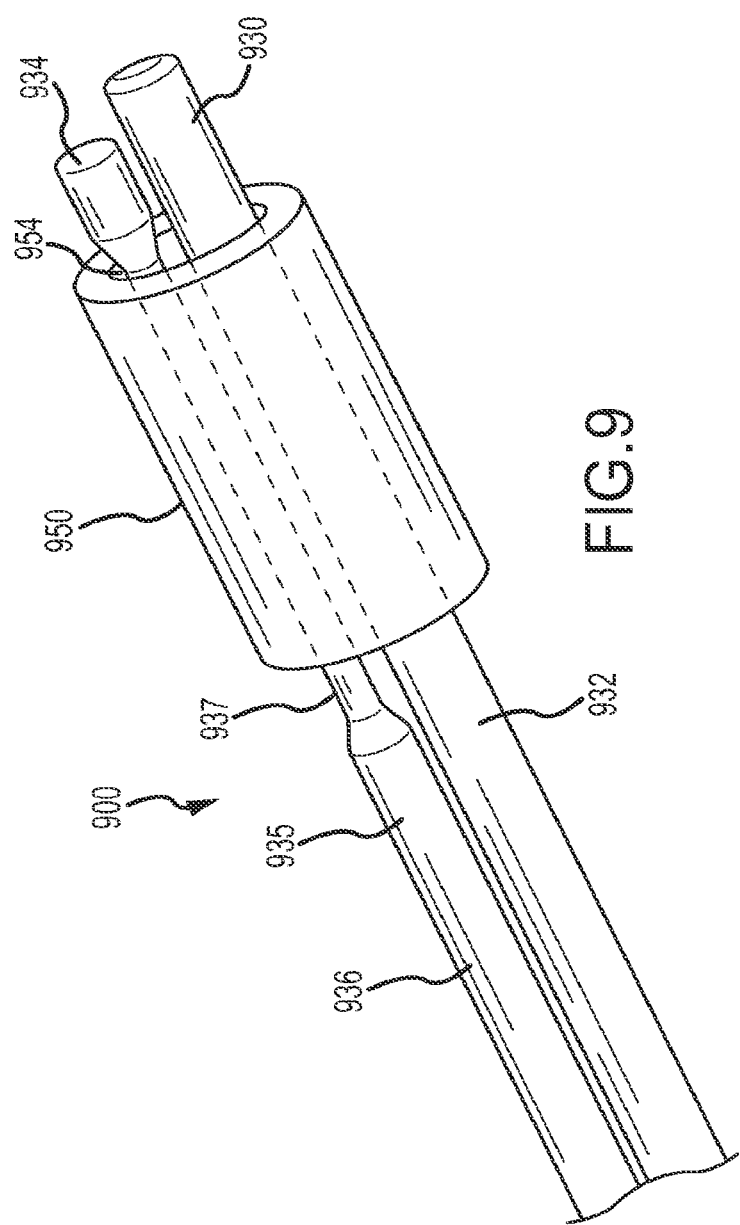
FIG. 9 shows a perspective side view of a vascular delivery system, in accordance with one or more exemplary implementations of the present disclosure.

According to some exemplary implementations, as shown in FIG. 9, a vascular delivery system 900 can include an implant hub 950 defining a port 954 having an inner cross-sectional dimension. An anchor wire 936 can extend through the port 954 such that an enlarged anchor portion 934 is positioned distal to the port 954 and the hub 950. The enlarged anchor portion 934 has an anchor cross-sectional dimension that is greater than a cross-sectional dimension of a proximal portion of the anchor wire. One or more control wires 932 can extend through the port 954 such that an engagement portion 930, at a distal or distalmost portion of each control wire 932, is positioned distal to the port 954 and the hub 950. The distal end 930 has an engagement cross-sectional dimension. The engagement portion 930 is retractable proximally relative to the anchor portion 934. The anchor portion 934 is configured to remain distal to the port 954 until the engagement portion 930 is retracted proximally past the port 954. According to some exemplary implementations, the inner cross-sectional dimension of the port 954 is less than the sum of the anchor cross-sectional dimension of the anchor portion 934 and the engagement cross-sectional dimension of the engagement portion 930.

According to some exemplary implementations, the anchor wire 936 includes a neck portion 937, proximal to the anchor portion 934, with a neck cross-sectional dimension less than the anchor cross-sectional dimension of the anchor portion 934. The anchor wire 936 also includes proximal portion 935, proximal to the neck portion 937, with a proximal cross-sectional dimension greater than the neck cross-sectional dimension of the neck portion 937. While in an engaged configuration, the hub 950 is located axially between the proximal portion 935 and the anchor portion 934. Axial motion of the hub 950 is limited in a distal direction by the anchor portion 934. Axial motion of the hub 950 is limited in a proximal direction by the proximal portion 934. Such limits can be eliminated by removal of the anchor wire 932.

According to some exemplary implementations, using an anchor wire 936 (e.g., of nitinol) with reduced neck cross section at the neck portion 937 through the implant hub 950 provides for ready deflection of the anchor portion 934 by the control wire 932 (e.g., of stainless steel), accompanied by active return of the anchor portion 934 toward the longitudinal axis for easy removal. The lower stiffness of the anchor wire 936 also reduces lateral friction forces against the control wire 932 for more reliable detachment from the implant hub 950 with concomitant lower tensile loads on the control wire 932.

According to some exemplary implementations, as shown in FIG. 10A-10C, a vascular delivery system 1000 can include an implant hub 1050 defining a port 1054 having an inner cross-sectional dimension. An anchor wire 1036 can extend through the port 1054 such that an enlarged anchor portion 1034 is positioned distal to the port 1054 and the hub 1050. The enlarged anchor portion 1034 has an anchor cross-sectional dimension that is greater than a cross-sectional dimension of a proximal portion of the anchor wire. One or more control wires 1032 can extend through the port 1054 such that an engagement portion 1030, at a distal or distalmost portion of each control wire 1032, is positioned distal to the port 1054 and the hub 1050. The distal end 1030 has an engagement cross-sectional dimension. The engagement portion 1030 is retractable proximally relative to the anchor portion 1034. The anchor portion 1034 is configured to remain distal to the port 1054 until the engagement portion 1030 is retracted proximally past the port 1054. According to some exemplary implementations, the inner cross-sectional dimension of the port 1054 is less than the sum of the anchor cross-sectional dimension of the anchor portion 1034 and the engagement cross-sectional dimension of the engagement portion 1030.

According to some exemplary implementations, the anchor wire 1036 includes a neck portion 1037, proximal to the anchor portion 1034, with a neck cross-sectional dimension less than the anchor cross-sectional dimension of the anchor portion 1034. The anchor wire 1036 also includes proximal portion 1035, proximal to the neck portion 1037, with a proximal cross-sectional dimension greater than the neck cross-sectional dimension of the neck portion 1037.

According to some exemplary implementations, the anchor wire 1036 has a first longitudinally extending flat surface 1035 and the control wire 1032 has a second longitudinally extending flat surface 1031, facing the first longitudinally extending flat surface of the anchor wire 1036. Each of the anchor wire 1036 and the control wire 1032 can include a flat surface and a curved surface. When arranged with flat surfaces facing each other, the control wire 1032 and the anchor wire 1036 can create a geometric shape in cross-section. For example, each of the anchor wire 1036 and the control wire 1032 can form a semicircle in cross-section ("half round profile"), such that together they form a full circle in cross-section. An exemplary implementation utilizes half round profiles for the anchor and control wires and eliminates additional "dummy" wires of some exemplary delivery systems.

Using half round wire profiles for the control and anchor wires eliminates the need for a "dummy" wire in the delivery system. The "dummy" wire would be used to prohibit twisting of the control and anchor wires around each other over the length of the delivery shaft. Half round profiles can prohibit the twisting of one wire around another within the delivery system shaft. Half round profiles can further reduce frictional forces between the control and anchor wires themselves and the inner diameter of the delivery system. Half round profiles will also reduce the overall stiffness of the delivery system without sacrificing the strength of the critical control/anchor wire elements.

The substitution of half round and/or control wires for three round wires enables delivery with only two wires and potentially reduced friction and stiffness in the lumen of the delivery shaft. As shown in FIGS. 10B and 10C, proximally directed withdrawal of the control wire 1032 enables subsequent proximally directed withdrawal of the anchor wire 1036.

One exemplary system utilizes three 0.004 round wires that nearly fill the entire 0.010 lumen of the delivery shaft (third wire not shown as it resides in the delivery shaft proximal to the implant hub). Two half round wires with a major diameter of 0.008 inches and a minor diameter of 0.004 inches will allow for a 0.002 inches clearance circumferentially within the existing delivery shaft thereby reducing frictional forces without a reduction in the strength of the control/anchor wire elements. Reduced friction would be expected between the anchor/control wire elements themselves as well as the inner diameter of the delivery system. Reduced stiffness of the delivery system along its entire length would also be anticipated.

One exemplary delivery system moves three wires relative to one another sequentially through the use of the slider component in the delivery system handle. As the dummy wire is retracted first, friction against the anchor and control wires can tend to move them proximally increasing the locking force of the anchor and control with the implant hub. The control wire must therefore overcome additional tensile forces to be removed before the anchor wire can be finally released. The use of half-round anchor and control wires can mitigate some or all of the unwanted friction and locking forces.

According to some exemplary implementations, as shown in FIGS. 11A-11D, a vascular delivery system 1100 can include an implant hub 1150 defining a port 1154 having an inner cross-sectional dimension. An anchor wire 1136 can extend through the port 1154 such that an enlarged anchor portion 1134 is positioned distal to the port 1154 and the hub 1150. The enlarged anchor portion 1134 has an anchor cross-sectional dimension that is greater than a cross-sectional dimension of a proximal portion of the anchor wire. One or more control wires 1132 can extend through the port 1154 such that an engagement portion 1130, at a distal or distalmost portion of each control wire 1132, is positioned distal to the port 1154 and the hub 1150. The distal end 1130 has an engagement cross-sectional dimension. The engagement portion 1130 is retractable proximally relative to the anchor portion 1134. The anchor portion 1134 is configured to remain distal to the port 1154 until the engagement portion 1130 is retracted proximally past the port 1154. According to some exemplary implementations, the inner cross-sectional dimension of the port 1154 is less than the sum of the anchor cross-sectional dimension of the anchor portion 1134 and the engagement cross-sectional dimension of the engagement portion 1130.

According to some exemplary implementations, the anchor wire 1136 includes a neck portion 1137, proximal to the anchor portion 1134, with a neck cross-sectional dimension less than the anchor cross-sectional dimension of the anchor portion 1134. The anchor wire 1136 also includes proximal portion 1135, proximal to the neck portion 1137, with a proximal cross-sectional dimension greater than the neck cross-sectional dimension of the neck portion 1137. According to some exemplary implementations, the anchor wire 1136 has a first longitudinally extending flat surface 1135 and the control wire 1132 has a second longitudinally extending flat surface 1131, facing the first longitudinally extending flat surface of the anchor wire 1136.

According to some exemplary implementations, to further improve the performance of the half-round wire elements, a push-pull mechanism can be utilized. For example, the anchor wire 1136 can be positioned such that the anchor portion 1134 abuts the distal edge of the port 1154, as shown in FIG. 11A. The anchor portion 1134 can be maintained in such a position by a controllable or consistent proximally directed force on the anchor wire 1136. For example, a spring or other mechanism (e.g. in the handle, not shown) can provide a proximally directed force on the anchor wire 1136. As the anchor portion 1134 abuts the distal edge of the port 1154, the anchor portion 1134 or another portion of the anchor wire 1136 engages the control wire 1132, thereby pressing the engagement portion 1130 against the port 1154 to create friction or an interference fit there between. As shown in FIG. 11B, the anchor wire 1136 can be advanced distally by a user to unlock the interference fit of the anchor wire/control wire assembly in the hub 1150. Subsequently or simultaneously, the control wire 1132 can be retracted proximally from the hub 1150, as shown in FIG. 11C. Finally, the anchor wire 1136 can be pulled from the hub 1150, detaching the implant, as shown in FIG. 11D.

Figure 12A:
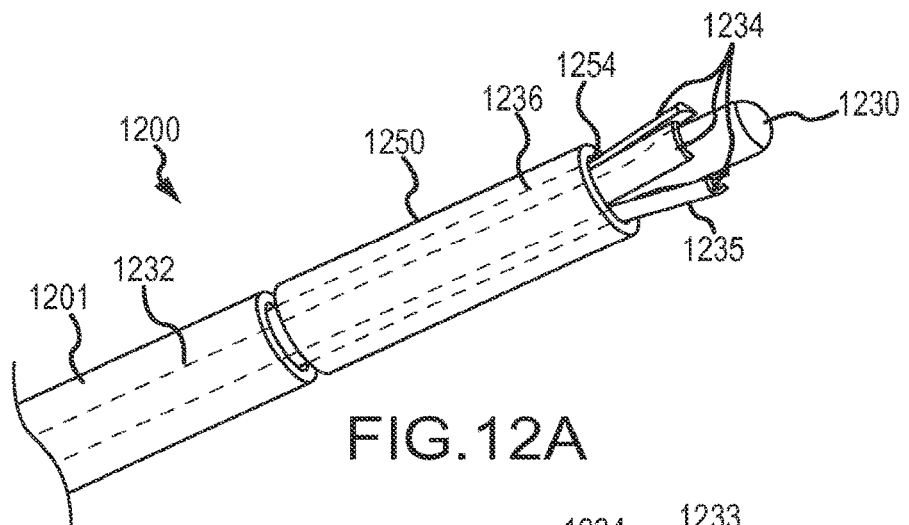
FIGS. 12A, 12B, and 12C show perspective side views of a vascular delivery system with an internal collet lock, in accordance with one or more exemplary implementations of the present disclosure.
Figure 12B:
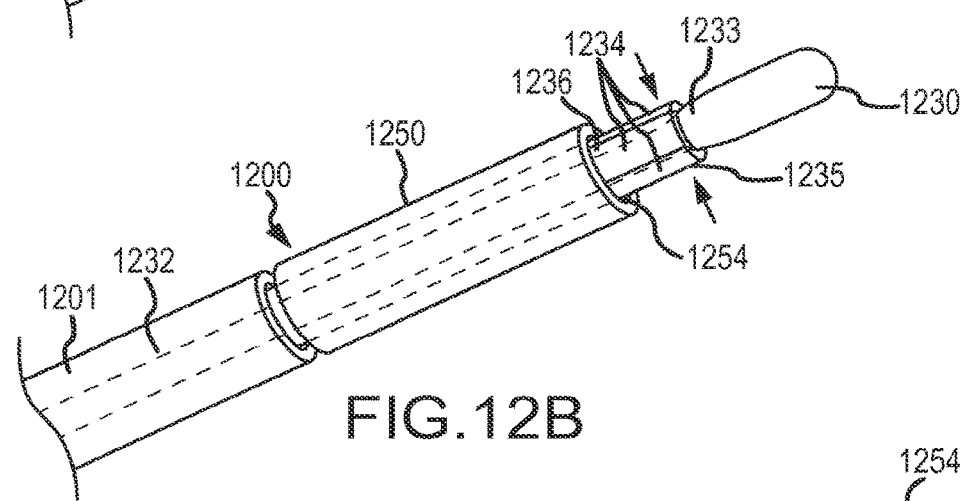
Figure 12C:
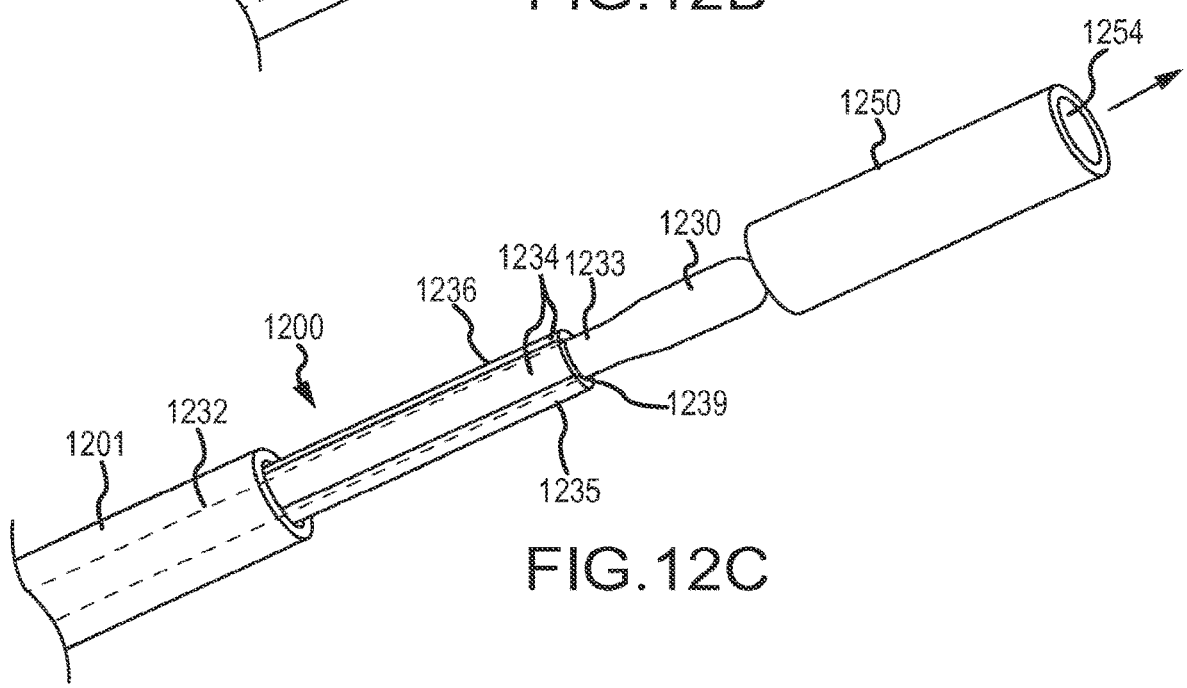

According to some exemplary implementations, as shown in FIGS. 12A-12C, a vascular delivery system 1200 can include an implant hub 1250 defining a port 1254 having an inner cross-sectional dimension. A shaft 1236 extends through the hub 1250 and includes a collet 1235 at a distal end of the shaft 1236, distal to the hub 1250 and the port 1254. The collet 1235 provides a plurality of extensions 1234. The extensions 1234 can be formed by kerf cuts into the shaft 1236 at the distal end thereof. A control wire 1232 extends through a lumen 1239 of the shaft 1236 and the collet 1235. The control wire 1232 has an engagement portion 1230, distal to at least a portion of the collet 1235, with an engagement cross-sectional dimension greater than the cross-sectional dimension of a portion of the control wire 1232 proximal of the engagement portion 1230. The collet 1235 can be in a flared state, with a flared outer cross-sectional dimension and a flared inner cross-sectional dimension. The collet 1235 can be in a relaxed state, with a relaxed outer cross-sectional dimension less than the flared outer cross-sectional dimension, and a relaxed inner cross-sectional dimension. The flared outer cross-sectional dimension and the relaxed outer cross-sectional dimension can be defined by the greatest radial cross-sectional dimension of the extensions 1234 in the respective state. The flared inner cross-sectional dimension and the relaxed inner cross-sectional dimension can be defined by the radial size of the lumen 1239 through the collet 1235.

As shown in FIGS. 12A and 12B, the engagement cross-sectional dimension of the engagement portion 1230 is greater than a relaxed inner cross-sectional dimension of the lumen 1239 at the collet 1235. Accordingly, when the engagement portion 1230 is moved proximally against the collet 1235, the extensions 1234 of the collet 1235 transition from the relaxed state to the flared state. According to some exemplary implementations, the inner cross-sectional dimension of the port 1254 is less than the flared outer cross-sectional dimension of the collet 1235. Accordingly, the shaft 1236 is prevented from moving proximally through an relative to the hub 1250 while in the flared state and wall the engagement portion 1230 abuts the extensions 1234 of the collet 1235. The collet 1235 is configured to remain distal to the port 1254 while in the flared state.

According to some exemplary implementations, the flared outer cross-sectional dimension is greater than the inner cross-sectional dimension of the port 1254 and the relaxed outer cross-sectional dimension is less than or equal to the inner cross-sectional dimension of the port 1254. According to some exemplary implementations, the collet 1235 includes a plurality of fingers extending from a proximal section of the shaft. According to some exemplary implementations, the collet 1235 is biased to assume the relaxed state when unconstrained.

With reference to FIGS. 12A, 12B, and 12C, an exemplary implementation includes a nitinol tube 1236, with a collet 1235 having multiple finger-like features 1234 cut (e.g., by laser) into the distal end and shape set straight (e.g., parallel to a longitudinal axis) when unconstrained. The nitinol tube 1236 is attached to the distal end of the delivery system shaft 120 and is slidable inside the hub 1250 of the implant. The finger features 1234 are deformed outwardly when an axially located spring loaded control wire 1232 with an enlarged tip 1230 is pulled back (proximally) into the fingers 1234, locking the implant and hub 1250 to the delivery system 1201 at the distal end of the inner hub 1250. When the control wire 1232 is advanced forward (distally), the fingers 1234 super-elastically recover to their straight configuration, allowing the control wire 1232 and nitinol tube to be slipped out of the implant hub 1250 thereby detaching the implant from the delivery system, as shown in FIG. 12C.

The substitution of the internal collet system for exemplary three round wires enables a single wire delivery system and potentially reduced friction and stiffness in the lumen of the delivery shaft. One exemplary three-wire system requires the relative motion of three separate wire elements during the detachment process over several centimeters. The internal collet system requires only one wire to be moved, and that movement can be limited to about 1 mm of travel. Since there is only one wire to be moved, its diameter can be increased to provide greater column stiffness for pushability.

According to some exemplary implementations, the control wire 1232 tip geometry can take a variety of forms, e.g., ball end, or tapered stub. The control wire 1232 and internal collet 1235 can be made more radiopaque by plating, or in the case of the control wire 1232, filling with precious metals thereby allowing greater fluoroscopic visibility during deployment/detachment.

Figure 13A:
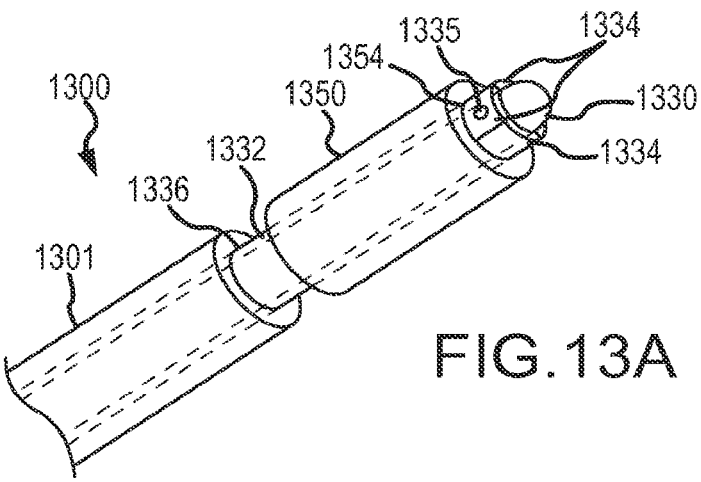
FIGS. 13A, 13B, and 13C show perspective side views of a vascular delivery system with a tube lock, in accordance with one or more exemplary implementations of the present disclosure.
Figure 13B:
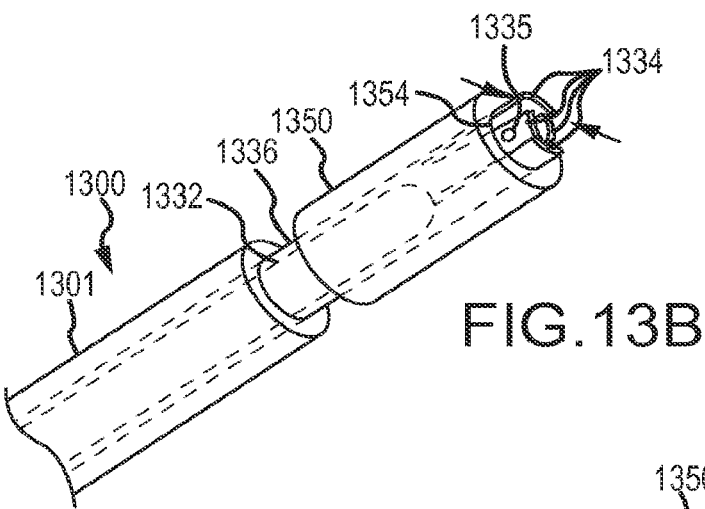
Figure 13C:
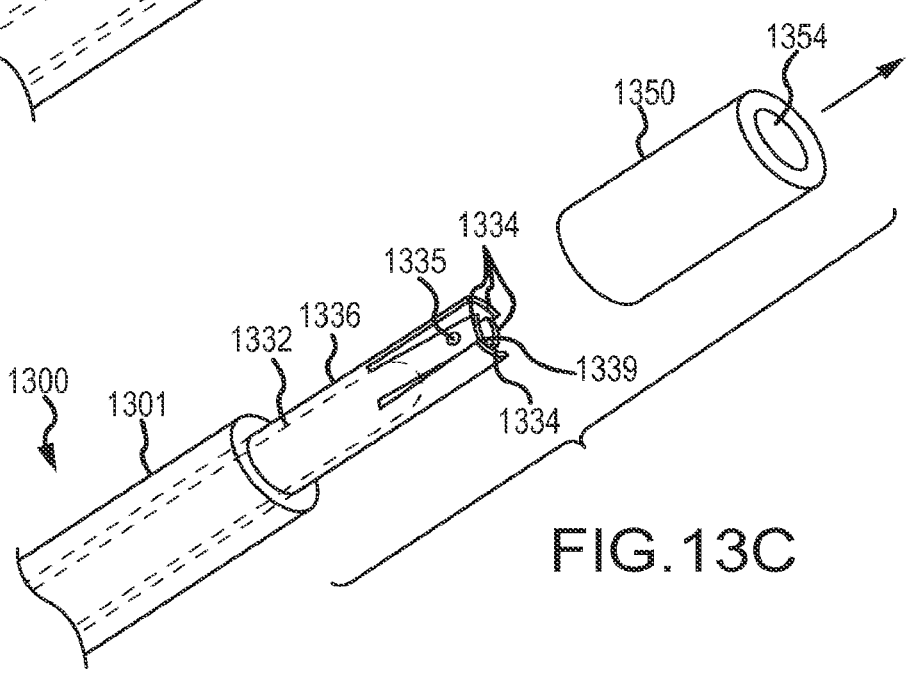

According to some exemplary implementations, as shown in FIGS. 13A-13C, a vascular delivery system 1300 can include an implant hub 1350 defining a port 1354 having an inner cross-sectional dimension. A shaft 1336 having an interference section including a plurality of extensions 1334, distal to the port 1354, having an extended state (FIG. 13A) with an extended inner cross-sectional dimension an extended outer cross-sectional dimension, and a relaxed state (FIG. 13B) with a relaxed inner cross-sectional dimension and a relaxed outer cross-sectional dimension less than the extended outer cross-sectional dimension. The flared outer cross-sectional dimension and the relaxed outer cross-sectional dimension can be defined by the greatest radial cross-sectional dimension of the extensions 1334 in the respective state, including measurement across protrusions 1335 that can be located on an outer surface of one or more of the extensions 1334. The protrusions 1335 can be formed at a distalmost end of the extensions 1334 or at a location proximal of the distalmost end of the extensions 1334. The protrusions 1335 can be solitary masses of material or patterned masses. The flared inner cross-sectional dimension and the relaxed inner cross-sectional dimension can be defined by the radial size of the lumen 1339 through the shaft 1336.

According to some exemplary implementations, a control wire 1332 extends through a lumen 1339 of the shaft 1336 and optionally past the extensions 1334. When an engagement portion 1330 of the control wire 1332 extends through the lumen 1339 at least to the location of one or more protrusions 1335 (the interference section), the shaft 1336 assumes the extended state, forming the extended outer cross-sectional dimension and the extended inner cross-sectional dimension. For example, the outer cross-sectional dimension of the engagement portion 1330 can be greater than the relaxed inner cross-sectional dimension of the shaft 1336, such that the engagement portion urges at least some of the extensions 1334 radially outward from the relaxed state to the extended state. The interference section is configured to remain distal to the port 1354 while in the extended state. According to some exemplary implementations, the extended cross-sectional dimension is defined by a distance between protrusions 1335 of a pair of extensions 1334, extending radially outward from a central axis of the system.

According to some exemplary implementations, proximal retraction of the engagement portion 1330 proximal to the interference section causes the extensions 1334 of the interference section to transition from the extended state to the relaxed state. According to some exemplary implementations, the interference section is biased to assume the relaxed state when unconstrained.

With reference to FIGS. 13A, 13B, and 13C, an exemplary implementation includes a nitinol tube 1336 with bilateral holes cut into the distal end of the tube. A fine platinum wire is then pushed through the holes and welded to form a small interference feature 1335 on the outer surface of the tube bilaterally. The platinum wire remaining in the inner diameter of the tube is sheared off with a mandrel. Laser cut slots are cut into the distal end on either side of the platinum beads forming finger like structures and shape set inward when unconstrained. The nitinol tube 1336 is attached to the distal end of the delivery system sheath 1301 and is slidable inside the hub 1350 of the implant. The finger features carrying the welded platinum beads are deformed outwardly when an axially located control wire 1332 is pushed (distally) beyond the length the fingers 1334, the beads locking the implant to the delivery system at the distal end of the inner hub 1350. When the control wire 1332 is pulled back (proximally) the fingers super-elastically recover to their inward configuration allowing the control wire 1332 and nitinol tube 1336 to be slipped out of the implant hub 1350 thereby detaching the implant from the delivery system.

The substitution of the tube lock system for three round wires enables a single wire delivery system and potentially reduced friction and stiffness in the lumen of the delivery shaft. One exemplary three-wire system requires the relative motion of three separate wire elements during the detachment process over several centimeters. The tube lock system requires only one wire to be moved, and that movement is limited to about 2 mm of travel. Since there is only one wire to be moved, its diameter can be increased to provide greater tensile strength for releasing the implant.

According to some exemplary implementations, the control wire 1332 and nitinol tube 1336 can be made more radiopaque by plating, or in the case of the control wire, filling with precious metals thereby allowing greater fluoroscopic visibility during deployment/detachment.

With reference to FIGS. 13A, 13B, and 13C, the interference features 1335 can be formed by welding of a variety of other materials. Alternately, the interference features can be made magnetic so that they will attract one another once the control wire 1332 is removed. In this exemplary implementation, the shape set nitinol tube 1336 is replaced with other lower modulus materials so that the interference features 1335 can be easily retracted to the mid-line by the influence of the magnetic field.

Figure 14D:
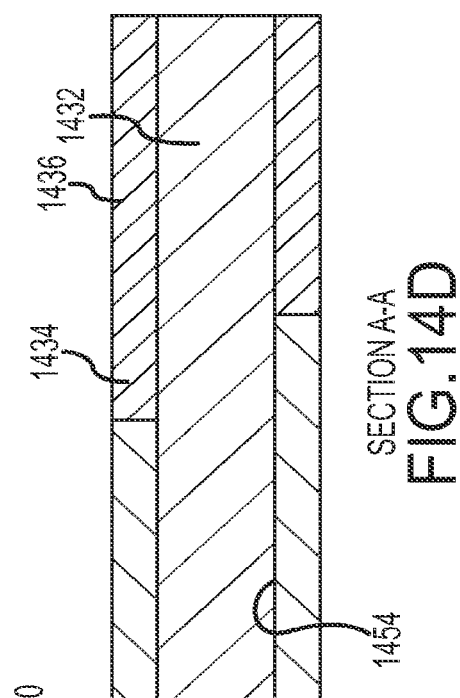
FIG. 14D shows a side-sectional view of a vascular delivery system with interlocking tubes, in accordance with one or more exemplary implementations of the present disclosure
Figure 14E:
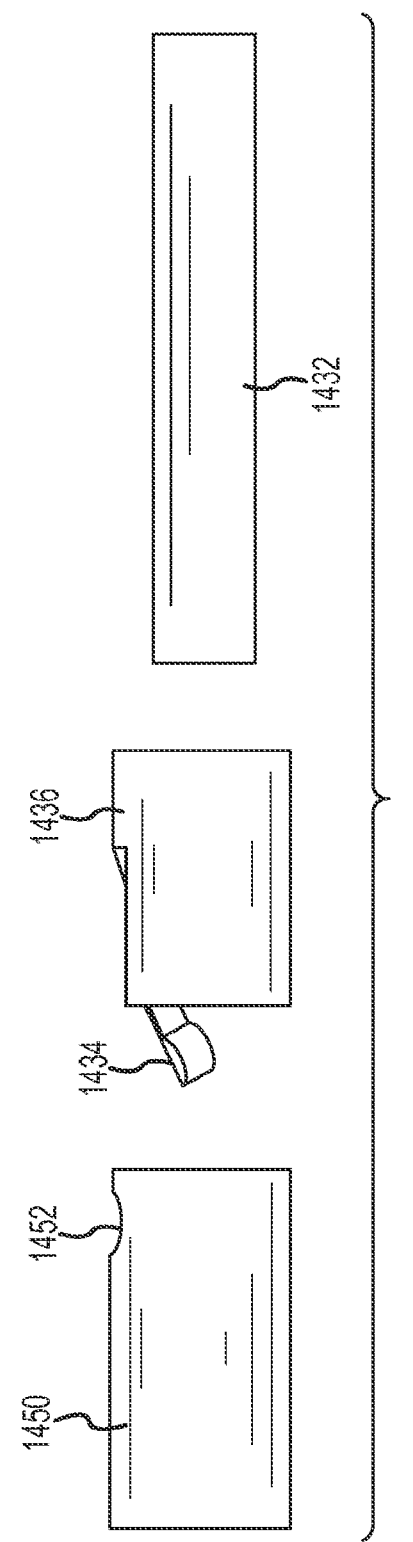
FIG. 14E shows a side view of a vascular delivery system with interlocking tubes, in accordance with one or more exemplary implementations of the present disclosure.

According to some exemplary implementations, as shown in FIGS. 14A-14E, a vascular delivery system 1400 can include an implant hub 1450 defining a lumen 1454 and a keyhole 1452 extending radially through a wall of the hub 1450. The system 1400 can further include a shaft 1436 having a appendage 1434 that is engaged within the keyhole 1452 in a deflected state and entirely within the lumen 1454 in a relaxed state. A control wire 1432 can extend within the lumen 1454, the control wire 1432 having an engagement portion that can be controllably retracted proximally relative to the appendage 1434. The engagement portion of the control wire 1432 deflects the appendage 1434 into the deflected state while the control wire 1432 is radially adjacent to the appendage 1434. The appendage 1434 is configured to achieve the relaxed state when the engagement portion of the control wire 1432 is retracted proximally past the appendage 1434, as shown in FIG. 14E. According to some exemplary implementations, the hub 1450 is secured relative to the shaft 1436 when the appendage 1434 is engaged within the keyhole 1452.

According to some exemplary implementations, two tubes are provided, one fixed to the delivery system, the other incorporated into implant. The delivery system tube 1436 is made of nitinol and has an appendage 1434 keyed for the second tube 1450. The delivery system tube 1436 is heat set such that the appendage 1434 protrudes into the inner diameter of the tubes, disaffecting the keyed lock. A mandrel is run through both tubes to deflect the appendage 1434 and affect the lock between both tubes. This creates a reliable locking system between the implant and delivery system with a simple disconnect. Only one wire/mandrel needs to move to effect detachment. The locking appendage/key can modified both in shape, and plurality.

According to some exemplary implementations, as shown in FIGS. 15A-15E, a vascular delivery system 1500 can include an implant hub 1550 defining a lumen 1554 and a keyhole 1552 extending radially through a wall of the hub 1550. The system 1500 can further include a shaft 1536 having first and second appendages 1534a and 1534b that are engaged within respective first and second keyholes 1552a and 1552b in a deflected state and entirely within the lumen 1554 in a relaxed state. A control wire 1532 can extend within the lumen 1554, the control wire 1532 having an engagement portion that can be controllably retracted proximally relative to the appendages 1534a,b. The engagement portion of the control wire 1532 deflects the appendages 1534a,b into the deflected state while the control wire 1532 is radially adjacent to the appendages 1534a,b. The appendages 1534a,b are configured to achieve the relaxed state when the engagement portion of the control wire 1532 is retracted proximally past the appendages 1534a,b, as shown in FIG. 15E. According to some exemplary implementations, the hub 1550 is secured relative to the shaft 1536 when the appendages 1534a,b are engaged within the keyholes 1552a,b.

According to some exemplary implementations, the second appendage 1534b is axially aligned with the first appendage 1534a. According to some exemplary implementations, the second appendage 1534b is axially offset relative to the first appendage 1534a. According to some exemplary implementations, the second appendage 1534b is radially across from the first appendage 1534a. According to some exemplary implementations, three or more appendages 1534 and corresponding keyholes 1552 are provided.

Figure 16A:
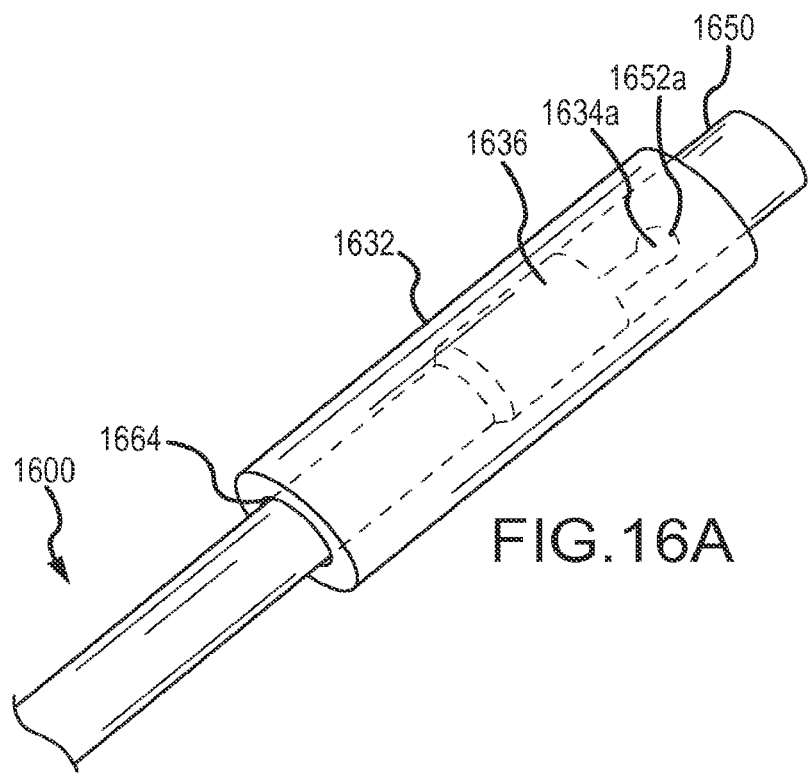
FIGS. 16A and 16B show perspective side views of a vascular delivery system with a paddle lock, in accordance with one or more exemplary implementations of the present disclosure.
Figure 16B:
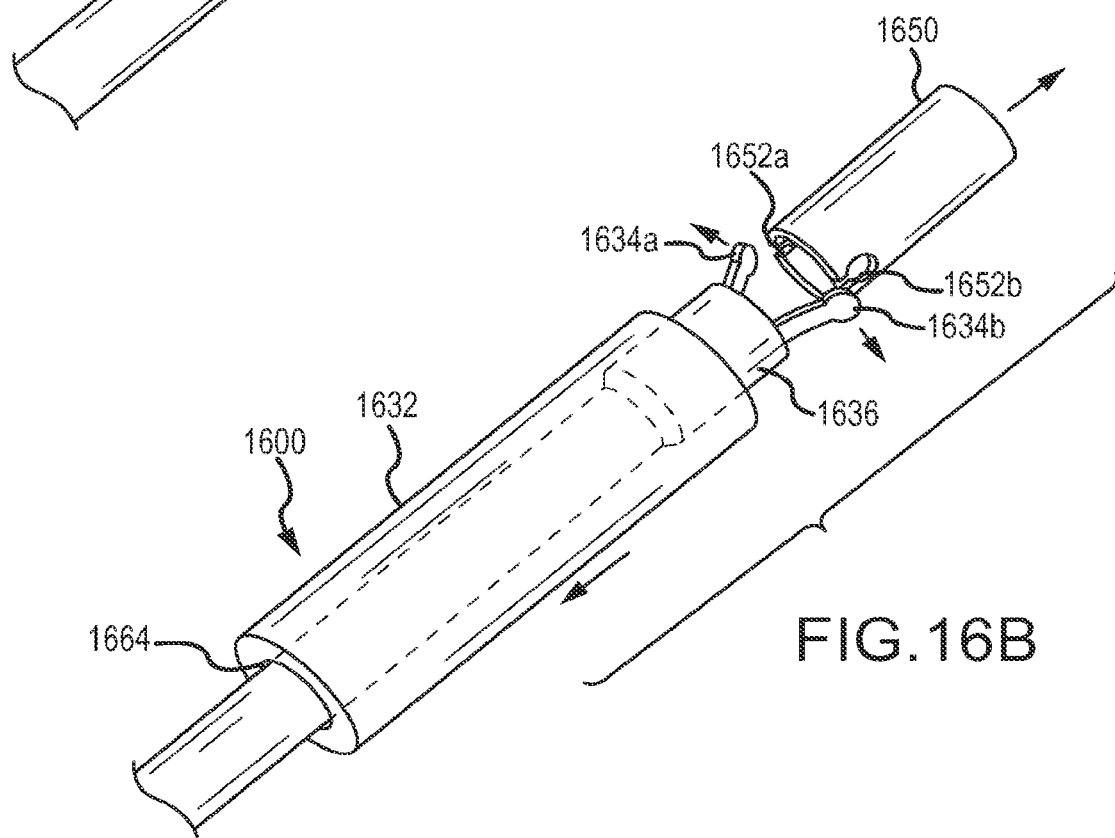

According to some exemplary implementations, as shown in FIGS. 16A and 16B, a vascular delivery system 1600 can include an implant hub 1650 defining one or more keyholes 1652 extending radially through a wall of the hub 1650 for engaging one or more appendages 1634. The system 1600 can further include a shaft 1636 having first and second appendages 1634a and 1634b that are engaged within respective first and second keyholes 1652a and 1652b in a deflected state and extending radially outwardly in a relaxed state. A constraining collar 1632 can extend over the appendages 1634a,b, thereby deflecting them from a relaxed state into the respective keyholes 1652a,b. The appendages 1634a,b are configured to achieve the relaxed state when the constraining collar 1632 is retracted proximally past the appendages 1634a,b, as shown in FIG. 16B. According to some exemplary implementations, the hub 1650 is secured relative to the shaft 1636 when the appendages 1634a,b are engaged within the keyholes 1652a,b while within the lumen 1664 of the constraining collar 1632.

According to some exemplary implementations, the second appendage 1634b is axially aligned with the first appendage 1634a. According to some exemplary implementations, the second appendage 1634b is axially offset relative to the first appendage 1634a. According to some exemplary implementations, the second appendage 1634b is radially across from the first appendage 1634a. According to some exemplary implementations, three or more appendages 1634 and corresponding keyholes 1652 are provided.

With reference to FIGS. 16A and 16B, an exemplary delivery system 1600 can include a tether shaft, attached to a nitinol tether 1650 at its distal end, that is in turn attached to the implant hub 1650 at its proximal end, and a delivery handle on the proximal end. The nitinol tether 1650 is designed with bilateral paddle features laser cut into the distal end and shape set to expand outwardly when unconstrained. The paddle features 1634 fit into similarly shaped keyholes 1652 cut into the outer band of the implant hub 1650 and are constrained by a thin polymer constraining collar 1632. When the constraining collar 1632 is retracted proximally, the paddles 1634 expand radially outwardly releasing the implant hub 1650 from the delivery system 1600.

An exemplary implementation provides a more reliable detachment mechanism for the implant. Anchoring the implant on the outer diameter of the hub allows for greater anchoring contact with the device. Since there is nothing required of the inner diameter, it can be eliminated, saving considerable space for lower profile devices. Because the device is delivered intravascularly, free recovery of the paddles at the time of deployment is possible. With respect to the two- or three-wire delivery systems, the possibility of jamming of the control and anchor wires under tension is reduced or eliminated.

According to some exemplary implementations, the paddle structures could have a variety of other shapes, e.g., rectangular, oval, or teardrop. The member that constrains the paddles (collar tube) could be made of a variety of other materials including metals. The collar tube can be machined with interlocking features to provide increased flexibility. The shape set nitinol paddle structures can be made more radiopaque by plating with gold or tantalum, allowing greater fluoroscopic visualization of detachment.

If the inner diameter of an exemplary device is preserved, a hollow lumen would allow for delivery of the device over a guidewire. This would provide and added safety feature as the implant could be snared even after full release of the implant from the delivery system using conventional snare technology. Alternatively, a microcoil, embolic spheres, or other materials could be delivered through the implant hub to the inside of the implant (as an aid to aneurysmal occlusion) following its deployment into the aneurysm and prior to final release to aid in the obstruction of the aneurysmal sac.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There can be many other ways to implement the subject technology. Various functions and elements described herein can be partitioned differently from those shown without departing from the scope of the subject technology. Various modifications to these configurations will be readily apparent to those skilled in the art, and generic principles defined herein can be applied to other configurations. Thus, many changes and modifications can be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes can be rearranged. Some of the steps can be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface can extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein can be embodied in a variety of other forms without departing from the spirit thereof. The accompanying claims and their equivalents are intended to cover such forms or modifications as would fall within the scope and spirit of the subject technology.

What is claimed is:

1. A vascular delivery system comprising:
   an implant having, at a proximal region, a first tube comprising a hub defining a first lumen having a first diameter, with a central axis, and a first keyhole extending radially through a wall of the hub;
   a second tube comprising a shaft defining a second lumen having a second diameter substantially the same as the first diameter, the shaft having a first appendage engaged within the first keyhole in a deflected state and entirely within the lumen in a relaxed state, wherein when the first appendage is engaged within the first keyhole, the first lumen and the second lumen are aligned and define a contiguous surface, and
   a control wire having an engagement portion configured to extend within the lumen and be controllably retracted proximally relative to the first appendage,
   wherein the engagement portion is configured to deflect the first appendage into the deflected state while the engagement portion is radially adjacent to the first appendage, and
   wherein the first appendage is configured to achieve the relaxed state when the engagement portion is retracted proximally past the first appendage.

2. The system of claim 1, wherein the hub is secured relative to the shaft when the first appendage is engaged within the first keyhole.

3. The system of claim 1, further comprising a second appendage of the shaft engaged within a second keyhole of the hub.

4. The system of claim 3, wherein the second appendage is axially aligned with the first appendage.

5. The system of claim 3, wherein the second appendage is axially offset relative to the first appendage.

6. A vascular delivery system comprising:
   an implant having, at a proximal region, a first tube comprising a hub with a first outer surface having a first outer diameter, a central axis, and a first keyhole extending radially into a wall of the hub;
   a second tube comprising a shaft defining second outer surface having a second outer diameter substantially the same as the first outer diameter, the shaft having a first appendage engaged within the first keyhole in a constrained state and radially away from the central axis and entirely out of the first keyhole in a relaxed state, wherein when the first appendage is engaged within the first keyhole, the first outer surface and the second outer surface are aligned and define a contiguous surface; and
   a constraining collar configured to extend over the first appendage and about the hub and be controllably retracted proximally relative to the first appendage,
   wherein the constraining collar is configured to deflect the first appendage into the constrained state while the constraining collar is covering the first appendage, and
   wherein the first appendage is configured to achieve the relaxed state when the constraining collar is retracted proximally past the first appendage.

7. The system of claim 6, wherein the hub is secured relative to the shaft when the first appendage is engaged within the first keyhole.

8. The system of claim 6, further comprising a second appendage of the shaft engaged within a second keyhole of the hub.

9. The system of claim 8, wherein the second appendage is axially aligned with the first appendage.

10. The system of claim 8, wherein the second appendage is axially offset relative to the first appendage.

11. A method of delivering a vascular implant comprising:
delivering, to a target location, an implant having a hub at a proximal end of the implant, the hub defining a first lumen having a first diameter, while (i) an appendage of a shaft engages a keyhole extending radially through a wall of the hub in an extended state, the shaft defining a second lumen having a second diameter substantially the same as the first diameter, and (ii) a control wire extends through a lumen defined by the shaft and the hub to hold the appendage in the extended state, wherein while the appendage engages the keyhole, the first lumen and the second lumen are aligned and define a contiguous surface;
retracting the control wire proximally until the appendage transitions radially inwardly to a relaxed state out of the keyhole and entirely within the lumen; and
retracting the shaft proximally away from the hub.

12. The method of claim 11, wherein the hub is secured relative to the shaft when the first appendage is engaged within the first keyhole.

13. The method of claim 11, wherein the shaft comprises a second appendage engaged within a second keyhole of the hub.

14. The method of claim 13, wherein the second appendage is axially aligned with the first appendage.

15. The method of claim 13, wherein the second appendage is axially offset relative to the first appendage.

16. A method of delivering a vascular implant comprising:
delivering, to a target location, an implant having a hub at a proximal end of the implant, the hub defining a first outer surface having a first outer diameter, while (i) an appendage of a shaft engages a keyhole extending radially through a wall of the hub in a constrained state, the shaft defining a second outer surface having a second outer diameter substantially the same as the first outer diameter, and (ii) a constraining collar extends over the appendage and about the hub to hold the appendage in the constrained state, wherein when the first appendage is engaged within the first keyhole, the first outer surface and the second outer surface are aligned and define a contiguous surface;
retracting the constraining collar proximally until the appendage transitions radially outwardly to a relaxed state out of the keyhole; and
retracting the shaft proximally away from the hub.

17. The method of claim 16, wherein the hub is secured relative to the shaft when the first appendage is engaged within the first keyhole.

18. The method of claim 16, wherein the shaft comprises a second appendage engaged within a second keyhole of the hub.

19. The method of claim 18, wherein the second appendage is axially aligned with the first appendage.

20. The method of claim 18, wherein the second appendage is axially offset relative to the first appendage.

* * * * *